(12) United States Patent
Starkebaum

(10) Patent No.: US 8,301,265 B2
(45) Date of Patent: Oct. 30, 2012

(54) SELECTIVE DEPTH ELECTRODE DEPLOYMENT FOR ELECTRICAL STIMULATION

(75) Inventor: Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1063 days.

(21) Appl. No.: 11/852,766

(22) Filed: Sep. 10, 2007

(65) Prior Publication Data
US 2009/0069803 A1  Mar. 12, 2009

(51) Int. Cl.
*A61N 1/00* (2006.01)

(52) U.S. Cl. ........... 607/116; 607/40; 607/132; 607/133

(58) Field of Classification Search .................... 607/40, 607/116, 132–133
See application file for complete search history.

(56) References Cited

U.S. PATENT DOCUMENTS

| | | | |
|---|---|---|---|
| 3,411,507 A | 11/1968 | Wingrove | |
| 3,862,627 A | 1/1975 | Hans, Sr. | |
| 4,633,889 A | 1/1987 | Talalla et al. | |
| 4,736,749 A | 4/1988 | Lundback | |
| 4,832,048 A | 5/1989 | Cohen | |
| 5,476,494 A | 12/1995 | Edell et al. | |
| 5,690,691 A | 11/1997 | Chen et al. | |
| 5,766,234 A | 6/1998 | Chen et al. | |
| 6,185,463 B1 | 2/2001 | Baudino | |
| 6,216,039 B1 | 4/2001 | Bourgeois | |
| 6,243,607 B1 | 6/2001 | Mintchev et al. | |
| 6,285,897 B1 | 9/2001 | Kilcoyne et al. | |
| 6,355,031 B1 | 3/2002 | Edwards et al. | |
| 6,405,067 B1 | 6/2002 | Mest et al. | |
| 6,456,865 B2 | 9/2002 | Samson | |
| 6,461,350 B1 | 10/2002 | Underwood et al. | |
| 6,506,190 B1 | 1/2003 | Walshe | |
| 6,529,778 B2 | 3/2003 | Prutchi | |
| 6,544,261 B2 | 4/2003 | Ellsberry et al. | |
| 6,606,523 B1 | 8/2003 | Jenkins | |
| 6,689,056 B1 | 2/2004 | Kilcoyne et al. | |
| 6,698,056 B1 | 3/2004 | Oretti et al. | |
| 6,754,536 B2 | 6/2004 | Swoyer et al. | |

(Continued)

FOREIGN PATENT DOCUMENTS

EP  0 318 789 B1  6/1989

(Continued)

OTHER PUBLICATIONS

Notification of Transmittal of the International Search Report and the Written Opinion of the International Searching Authority for corresponding patent application No. PCT/US2008/071404, mailed Dec. 4, 2008, (16 pages).

(Continued)

*Primary Examiner* — Nicole F Lavert

(57) ABSTRACT

The invention is directed toward stimulation of a selected tissue layer. A device is attached to a target tissue by applying vacuum pressure to a vacuum cavity of the device and advancing a needle into tissue within the vacuum cavity. The depth on the vacuum cavity is selected to permit deployment at the selected tissue layer. In one embodiment, the invention is directed toward an implantable medical device comprising a device housing defining a vacuum cavity, and a vacuum port for application of vacuum pressure to draw tissue into the vacuum cavity, an electrode that is movable into the vacuum cavity of the device housing to contact at least a portion of the tissue drawn into the vacuum cavity, and a lead comprising at least one conductor coupled to the electrode.

32 Claims, 12 Drawing Sheets

U.S. PATENT DOCUMENTS

| | | |
|---|---|---|
| 7,020,531 B1 | 3/2006 | Colliou et al. |
| 7,063,698 B2 | 6/2006 | Whayne et al. |
| 7,104,986 B2 | 9/2006 | Hovda et al. |
| 7,146,225 B2 | 12/2006 | Guenst et al. |
| 7,201,290 B2 | 4/2007 | Mehus et al. |
| 7,206,641 B2 | 4/2007 | Ignagni et al. |
| 2002/0091421 A1 | 7/2002 | Greenberg et al. |
| 2002/0103424 A1 | 8/2002 | Swoyer et al. |
| 2005/0043601 A1 | 2/2005 | Kilcoyne et al. |
| 2005/0090873 A1 | 4/2005 | Imran |
| 2005/0209653 A1* | 9/2005 | Herbert et al. ............ 607/40 |
| 2006/0089690 A1 | 4/2006 | Gerber |
| 2006/0095032 A1 | 5/2006 | Jackson et al. |
| 2006/0111753 A1 | 5/2006 | Imran et al. |
| 2006/0265021 A1 | 11/2006 | Herbert et al. |
| 2007/0021736 A1 | 1/2007 | Johnson |

FOREIGN PATENT DOCUMENTS

| | | |
|---|---|---|
| WO | WO 87/04081 | 7/1987 |
| WO | WO 00/59376 | 10/2000 |
| WO | WO 02/087657 A2 | 11/2002 |
| WO | WO 2006/118927 A1 | 11/2006 |

OTHER PUBLICATIONS

Goyal et al., "Gastrointestinal electrical stimulation (GES) can be performed safely with endoscopically placed electrodes", American Journal of Gastroenterology 96(9), 2001, abstract, 1 pg.

* cited by examiner

SELECTIVE DEPTH ELECTRODE DEPLOYMENT FOR ELECTRICAL STIMULATION

TECHNICAL FIELD

The invention relates to implantable medical devices and, more particularly, implantable medical devices for electrical stimulation.

BACKGROUND

Gastroparesis is an adverse medical condition in which normal gastric motor function is impaired. Gastroparesis results in delayed gastric emptying as the stomach takes too long to empty its contents. Typically, gastroparesis results when muscles within the stomach or intestines are not working normally, and movement of food through the stomach slows or stops. Patients with gastroparesis typically exhibit symptoms of nausea and vomiting, as well as gastric discomfort such as bloating or a premature or extended sensation of fullness, i.e., satiety. The symptoms of gastroparesis may be at least in part the result of impaired gastric myoelectric activity and reduced gastric motility. Gastroparesis generally causes reduced food intake and subsequent weight loss, and can adversely affect patient health.

Obesity is a serious health problem for many people. Patients who are overweight often have problems with mobility, sleep, high blood pressure, and high cholesterol. Some other serious risks also include diabetes, cardiac arrest, stroke, kidney failure, and mortality. In addition, an obese patient may experience psychological problems associated with health concerns, social anxiety, and generally poor quality of life.

Electrical stimulation of the gastrointestinal tract has been used to treat symptoms of gastroparesis and obesity. For example, electrical stimulation of the gastrointestinal tract, and especially the stomach, is effective in suppressing symptoms of nausea and vomiting secondary to gastroparesis. As another example, electrical stimulation of the gastrointestinal tract may be used to treat obesity by inducing a sensation of fullness to prevent excessive food intake and/or increasing gastric motility to reduce caloric absorption. Typically, electrical stimulation involves the use of electrodes implanted in the wall of a target organ, e.g., the stomach. The electrodes are electrically coupled to an implanted or external electrical stimulator, e.g., via implanted or percutaneous leads. The stimulator delivers a stimulation signal to the patient via the electrodes.

SUMMARY

In general, the invention is directed to deployment of electrical stimulation and/or sensing electrodes within the tissue of a patient. An electrode may be deployed at a selected depth within the tissue. The selected depth may correspond to a selected layer of the tissue at which stimulation will be delivered or an electrical signal sensed. An electrode assembly may be attached to a target tissue site by applying vacuum pressure to a vacuum cavity of the device, and then advancing an electrode into tissue that is drawn into the vacuum cavity.

The depth of the vacuum cavity may be selected to permit deployment of the electrode at a selected tissue layer. The height at which the electrode is deployed relative to the depth of the vacuum cavity may also be selected to permit deployment at a selected tissue layer. The electrode may be a needle electrode, which will be described for purposes of example. The needle electrode may electrically couple a stimulator or electrical sensing device to the tissue layer, e.g., via an implantable lead coupled to the needle. In addition, the needle electrode may serve as a fixation device to securely attach the electrode assembly to the target tissue site.

An electrode assembly may include multiple cavities having different depths selected to capture different tissue layers for deployment of a needle electrode. Multiple needle electrodes may be deployed using the multiple vacuum cavities, permitting deployment of multiple needle electrodes at different tissue layers. In addition, a needle electrode may extend into a single cavity or multiple cavities within a given electrode assembly.

In other cases, an electrode assembly may have a single vacuum cavity with a depth selected to capture a particular tissue layer for needle electrode deployment. A surgeon may select an electrode assembly from a set of electrode assembly devices with different vacuum cavity depths. Hence, a stimulator or electrical sensing device may be coupled to two or more needle electrodes in a single electrode assembly, or needle electrodes associated with different electrode assemblies. In either case, the needle electrodes may be deployed at selected depths within a target tissue site or sites.

Bipolar or multipolar electrode arrangements may be formed by multiple needle electrodes within a single electrode assembly or multiple needle electrodes in different electrode assemblies. Each of the needle electrodes may be coupled to respective implantable leads to receive electrical stimulation energy from an implantable or external stimulator or an electrical sensing device. In some embodiments, an electrode assembly may be a self-contained, leadless stimulator including both the stimulator electronics and needle electrodes.

In one embodiment, the invention is directed to an implantable medical device comprising a device housing defining a vacuum cavity, and a vacuum port for application of vacuum pressure to draw tissue into the vacuum cavity, an electrode that is movable into the vacuum cavity of the device housing to contact at least a portion of the tissue drawn into the vacuum cavity, and a lead comprising at least one conductor coupled to the electrode.

In another embodiment, the invention is directed to a system comprising an electrical stimulator, an electrode assembly comprising a housing defining a vacuum cavity, and a vacuum port for application of vacuum pressure to draw tissue into the vacuum cavity, an electrode that is movable into the vacuum cavity of the housing to contact at least a portion of the tissue drawn into the vacuum cavity, and a lead comprising at least one conductor that electrically couples the electrical stimulator to the electrode.

In yet another embodiment, the invention is directed to a method comprising applying vacuum pressure to a vacuum cavity in an electrode assembly housing to draw tissue into the vacuum cavity, advancing an electrode that is movable into the vacuum cavity of the housing to contact at least a portion of the tissue drawn into the vacuum cavity, wherein the electrode is coupled to at least one conductor in a lead and the lead is coupled to an electrical stimulator, and delivering electrical stimulation from the electrical stimulator to the tissue via the lead and the electrode.

In yet another embodiment, the invention is directed to an implantable medical device comprising a device housing defining first and second vacuum cavities, and one or more vacuum ports for application of vacuum pressure to draw tissue into at least one of the first and second vacuum cavities, and an electrode that is movable into at least one of the vacuum cavities of the device housing to contact the tissue drawn into the respective vacuum cavity.

In yet another embodiment, the invention is directed to a method comprising applying vacuum pressure to at least one of a first and second vacuum cavity in an electrode assembly housing to draw tissue into the respective vacuum cavity, advancing an electrode that is movable into at least one of the first and second vacuum cavities of the housing to contact the tissue drawn into the respective vacuum cavity, and delivering electrical stimulation to the tissue via the electrode.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
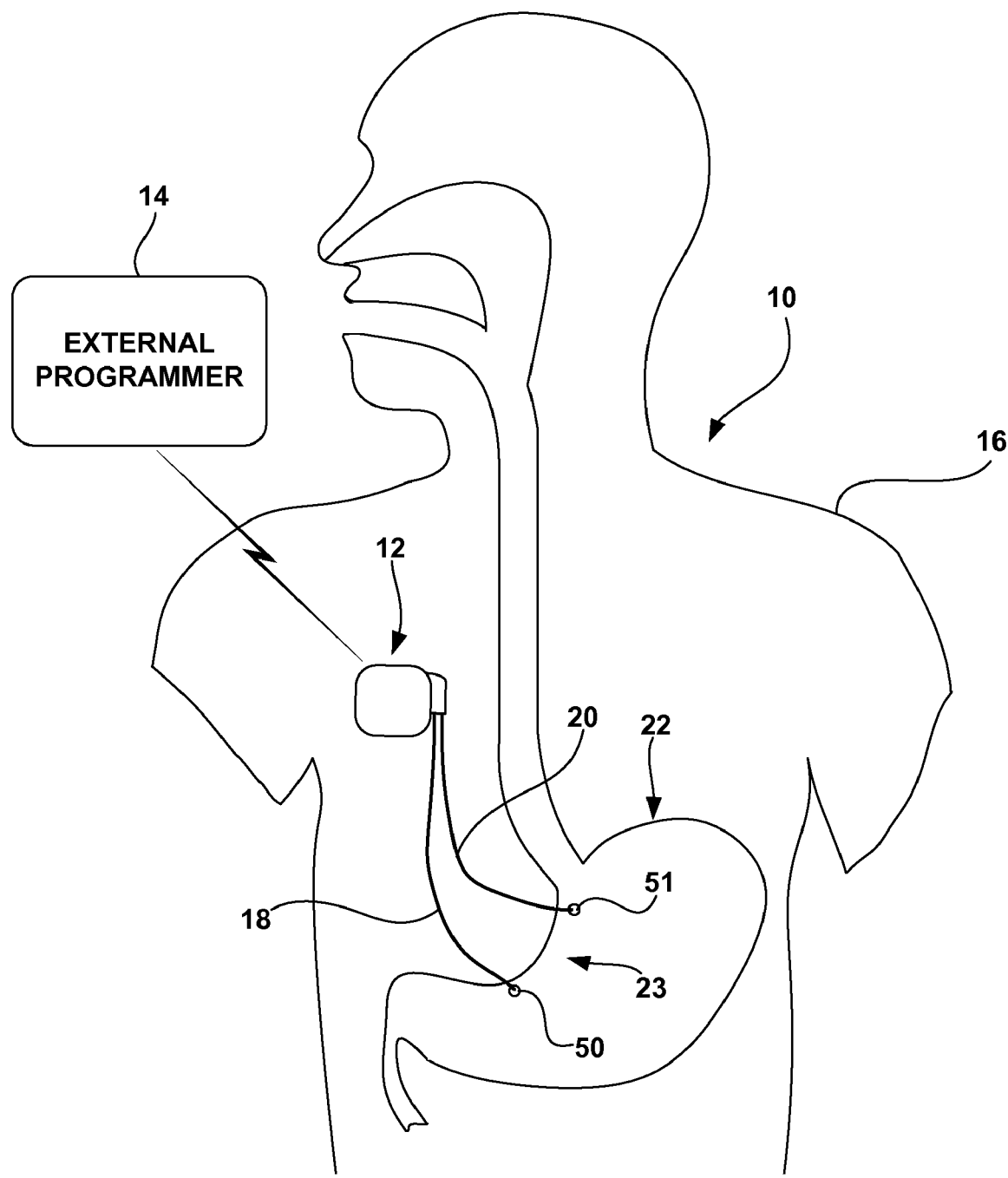
FIG. 1 is a schematic diagram illustrating an example implantable gastric stimulation system.

FIG. 1 is a schematic diagram illustrating an example implantable gastric stimulation system 10. System 10 delivers gastric stimulation therapy to patient 16 in the form of electrical stimulation. Patient 16 ordinarily will be a human patient. In some cases, however, the invention may be applied to non-human patients. While gastric stimulation therapy is shown to be delivered to stomach 22, the therapy may be delivered to other portions of patient 16, such as the duodenum or other portions of the gastrointestinal tract. In addition, the invention may be applied to other tissue sites or other therapies in which it may be advantageous to deliver electrodes within tissue layers, including delivery of electrodes at selected depths within tissue of the patient. Accordingly, the invention may be applicable to a variety of electrical stimulation therapies, such as spinal cord stimulation, pelvic floor stimulation, peripheral nerve stimulation, deep brain stimulation, muscle stimulation, or the like. In some embodiments, the invention may be applied to substantially hollow organs or tissues, such as the gastrointestinal tract, heart, large vessels, or aortas.

Electrical stimulation therapies may be configured to deliver electrical stimulation therapy to patients to treat a variety of symptoms or conditions such as chronic pain, tremor, movement disorders such as Parkinson's disease, brain seizures (e.g., associated with epilepsy), urinary or fecal incontinence, sexual dysfunction, nausea, obesity or gastroparesis. In accordance with various embodiments of this disclosure, electrodes may be deployed proximate to the spinal cord, pelvic nerves including sacral, pudendal or other nerves, stomach, intestines, muscles, peripheral nerves, or within the brain of a patient. Therefore, gastric stimulation therapy should be considered illustrative and non-limiting of the various applications of the invention as broadly embodied and described in this disclosure.

Further, the invention is not limited to stimulation therapies. In some embodiments, the system may include an electrical sensing device, for example, to measure biopotentials or bioimpedance. An electrical sensing device may be included in addition or as an alternative to an electrical stimulator. For example, a stimulation and sensing combination device may be used to deliver stimulation therapy and measure impedance, current, voltage or other electrical parameters. A combined stimulation and sensing device or a dedicated sensing device may be configured to record a variety of biopotential or bioimpedance values, e.g., for storage and/or telemetry to an external device. Stimulation therapy should be considered illustrative and non-limiting of the various applications of the invention as broadly embodied and described in this disclosure.

As shown in FIG. 1, system 10 may include a medical device 12 and a programmer 14, both shown in conjunction with a patient 16. Medical device 12 will be described herein as an implantable medical device (IMD) for purposes of example. However, medical device 12 is not limited to implantable devices and, in some embodiments, may be an external device, such as an external electrical stimulator. For example, in some embodiments, electrodes deployed as described in this disclosure may be coupled to an external stimulator via percutaneous leads. Hence, the stimulator may be fully implantable or external and the leads may be fully implantable or partially implantable.

IMD 12 includes a signal generator that generates electrical stimulation pulses or continuous stimulation signals. Electrical stimulation pulses may be characterized by pulse parameters such as amplitude, pulse width and pulse rate (frequency), one or more of which may be selected to address a particular therapeutic application, such as gastric stimulation for gastroparesis or obesity. More generally, the electrical stimulation may be selected, e.g., by configuration of appropriate parameters, to treat diseases or disorders treatable by at least one of gastric stimulation, spinal cord stimulation, deep brain stimulation, pelvic stimulation or peripheral nerve stimulation. In addition, the electrical stimulation may be selected to treat at least one of pain, movement disorders, brain seizures, urinary or fecal incontinence, sexual dysfunction, nausea, obesity or gastroparesis.

In some embodiments, system 10 may further include a drug delivery device that delivers drugs or other agents to the patient. One or more implantable leads 18, 20 carry the electrical stimulation signals from IMD 12 to stomach 22. In other embodiments, IMD 12 may be formed as an RF-coupled system in which an external controller provides both control signals and inductively coupled power to IMD 12 within patient 16.

Leads 18, 20 each include one or more electrode assemblies 50, 51 for delivery of electrical stimulation signals to stomach 22. In some embodiments, electrode assemblies 50, 51 may be self-contained stimulation devices, each of which may include a signal generator. In embodiments in which electrode assemblies 50, 51 are stimulation devices, electrode assemblies 50, 51 may be in wireless communication with IMD 12 rather than electrically coupled via leads 18, 20. In such embodiments, IMD 12 may function as a controller to control stimulation delivery via electrode assemblies 50, 51 in a synchronized manner. In other embodiments in which electrode assemblies 50, 51 include signal generators, electrode assemblies 50, 51 may each include telemetry modules to allow communication with an external controller and/or direct communication between electrode assemblies 50, 51. In such embodiments, IMD 12 may be an optional component of therapy system 10. Thus, any of the components, functions, or characteristics described with respect to IMD 12 may be incorporated into and/or performed by electrode assemblies 50, 51.

Although the electrical stimulation signals may be delivered to other areas within the gastrointestinal tract, such as the esophagus, duodenum, small intestine, or large intestine, delivery of stimulation signals to stomach 22 will generally be described in this disclosure for purposes of illustration. In the example of FIG. 1, electrode assemblies 50, 51 are placed in the lesser curvature 23 of stomach 22. Alternatively, or additionally, electrode assemblies 50, 51 may be placed in the greater curvature of stomach 22 or at some other location around stomach 22. As will be described in further detail, electrode assemblies 50, 51 may be configured to deploy one or more electrodes within tissue associated with the stomach wall. In some embodiments, electrode assemblies 50, 51 may be configured to deploy electrodes at selected depths or within selected tissue layers of the stomach wall. For certain therapies and/or patients, stimulation efficacy may be dependent upon which layer of stomach wall 58 is stimulated. Accordingly, selective depth deployment of electrodes via electrode assemblies 50, 51 may be desirable.

IMD 12 delivers electrical stimulation according to stimulation parameters stored within IMD 12. For example, various pulse widths, current or voltage amplitudes, pulse rates, and duty cycles may be stored within IMD 12 to define the stimulation signals delivered by IMD 12. In some embodiments, stimulation parameters may further include electrode combinations and polarities in the event leads 18, 20 provide multiple electrode positions. Such parameters may programmed into IMD 12 prior to implantation. Alternatively, or additionally, such parameters may be programmed into IMD 12 following implantation by an external programmer or controller via wireless telemetry. For example, an external patient programmer or physician programmer, or both, may be used automatically or manually to select programs, load new programs, and/or adjust parameters for operation of IMD 12.

IMD 12 may be constructed with a biocompatible housing, such as titanium, stainless steel, or a polymeric material, and may be surgically implanted within patient 16. The implantation site may be a subcutaneous location in the side of the lower abdomen or the side of the lower back. IMD 12 is housed within the biocompatible housing, and includes components suitable for generation of electrical stimulation signals. As mentioned above, IMD 12 may be responsive to an external programmer 14, such as a patient programmer or physician programmer, that generates control signals to adjust stimulation parameters. In a further embodiment, mentioned above, IMD 12 may be formed as an RF-coupled system in which programmer 14, alone or in combination with another external device, provides both control signals and inductively coupled power to an implanted signal generator.

Electrical leads 18 and 20 may be flexible and include one or more internal electrical conductors that are electrically insulated from body tissues and terminated with respective electrode assemblies 50 and 51 at the distal ends of the respective leads. The conductors may be formed as axial conductors or coiled conductors. Leads 18, 20 may define inner lumens to accommodate a removable stylet for manipulation and positioning of the leads. The leads may be surgically or percutaneously tunneled to stimulation sites on stomach 22. The proximal ends of leads 18 and 20 may be electrically coupled to the signal generator of IMD 12 via internal conductors to conduct the stimulation signals to stomach 22 via electrode assemblies 50, 51.

In certain embodiments, electrode assemblies 50, 51 may form a bipolar pair of electrodes. For example, each electrode assembly 50, 51 may include one electrode of a bipolar pair formed between the electrode assemblies. Alternatively, IMD 12 may carry a reference electrode to form an "active can" arrangement, in which one or both of electrode assemblies 50, 51 are unipolar electrodes referenced to the electrode associated with the IMD. The housing of implantable IMD 12 may itself serve as a reference electrode. A variety of polarities and electrode arrangements may be used. Again, each lead 18, 20 may coupled to a single electrode or an array of electrodes carried by electrode assemblies 50, 51, permitting selection of different electrode combinations and polarities among the leads for delivery of stimulation.

Again, the stimulation signals delivered by IMD 12 may be characterized by stimulation parameters, such as pulse width, voltage or current amplitude, and pulse rate. Such stimulation parameters may be fixed, adjusted in response to sensed physiological conditions within or near stomach 22, or adjusted in response to patient or physician input entered via programmer 14. For example, in some embodiments, patient 16 may be permitted to adjust stimulation amplitude, pulse width, or pulse rate and turn stimulation on and off via programmer 14.

Programmer 14 may transmit instructions to IMD 12 via wireless telemetry. Accordingly, IMD 12 includes telemetry electronics to communicate with programmer 14. Programmer 14 may be a small, battery-powered, portable device that accompanies patient 16 throughout a daily routine. Programmer 14 may have a simple user interface, such as a set of buttons or a keypad, and a display or lights. Programmer 14 may be a hand-held device configured to permit activation of stimulation and adjustment of stimulation parameters.

Alternatively, programmer 14 may form part of a larger device including a more complete set of programming features including complete parameter modifications, firmware upgrades, data recovery, or battery recharging in the event IMD 12 includes a rechargeable battery. Programmer 14 may be a patient programmer, a physician programmer, or a patient monitor. In some embodiments, programmer 14 may be a general purpose device such as a cellular telephone, a wristwatch, a personal digital assistant (PDA), or a pager.

In some embodiments, system 10 may include multiple IMDs 12 or multiple leads 18, 20 to stimulate a variety of regions of stomach 22. Stimulation delivered by the multiple IMDs may be coordinated in a synchronized manner or performed without communication between stimulators. As an example, one IMD may control other stimulators by wireless telemetry, all stimulators may be controlled by programmer 14, or the stimulators may act autonomously subject to parameter adjustment or download by programmer 14. Also, the electrodes may be located in a variety of sites on the stomach, or elsewhere in the gastrointestinal tract, dependent on the particular therapy or the condition of patient 16.

Figure 2:
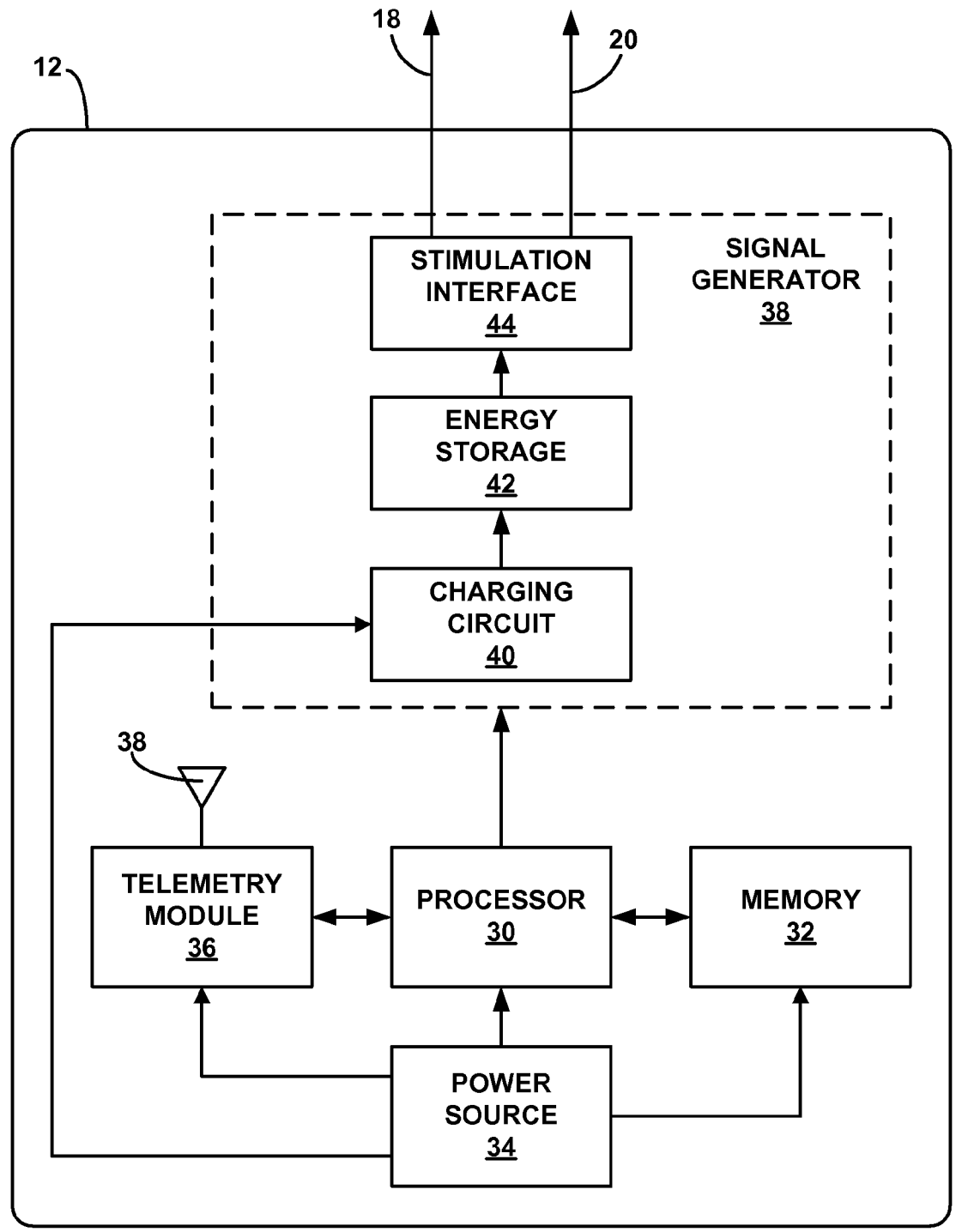
FIG. 2 is a block diagram illustrating exemplary functional components of the implantable medical device of FIG. 1.

FIG. 2 is a block diagram illustrating exemplary functional components of IMD 12. In the example of FIG. 2, IMD 12 may include a processor 30, memory 32, power source 34, telemetry module 36, and signal generator 38. Telemetry module 36 may permit communication with programmer 14 for transfer of data and adjustment of stimulation parameters. Alternatively, in some embodiments, IMD 12 may exclude telemetry module 36, in which case all stimulation parameters may be preset and fixed within the IMD. Exclusion of telemetry module 36 may be desirable in some applications to achieve reductions in the size and power consumption of IMD 12.

Processor 30 controls operation of IMD 12 and may include one or more microprocessors, digital signal processors (DSPs), application-specific integrated circuits (ASICs), field-programmable gate arrays (FPGAs), or other digital logic circuitry. Memory 32 may include any magnetic, electronic, or optical media, such as random access memory (RAM), read-only memory (ROM), electronically-erasable programmable ROM (EEPROM), flash memory, or the like. Memory 32 may store program instructions that, when executed by processor 30, cause the processor to perform the functions ascribed to it herein. For example, memory 32 may store instructions for processor 30 to execute to support control of telemetry module 36 and signal generator 38.

Telemetry module 36 may include a transmitter and receiver to permit bi-directional communication between IMD 12 and programmer 14. In this manner, programmer 14 may transmit commands to IMD 12 and receive status and operational information from IMD 12. Telemetry module 36 may include an antenna 38 that may take on a variety of forms. For example, antenna 38 may be formed by a conductive coil or wire embedded in a housing associated with IMD 12. Alternatively, antenna 38 may be mounted on a circuit board carrying other components of IMD 12 or take the form of a circuit trace on the circuit board. If IMD 12 does not include a telemetry module 36, a magnetic reed switch may be provided in a circuit between power source 34 and the other components of the IMD so that, with the aid of an external magnet, the IMD may be turned on at the time it is placed in the patient.

Power source 34 may take the form of a battery and power circuitry. In some embodiments, power source 34 may be rechargeable via induction or ultrasonic energy transmission and include an appropriate circuit for recovering transcutaneously received energy. For example, power source 34 may include a secondary coil and a rectifier circuit for inductive energy transfer. In other embodiments, power source 34 may not include any storage element and IMD 12 may be fully powered via transcutaneous inductive energy transfer.

Signal generator 38 produces an electrical stimulation signal with parameters selected to treat a particular disease or disorder of patient 16. As shown in FIG. 2, signal generator 38 may include a charging circuit 40, an energy storage device 42, and a stimulation interface 44. Charging circuit 40 converts energy supplied by power source 34 to charge energy storage device 42, which may be a capacitor. Stimulation interface 44 amplifies and conditions charge from energy storage device 42 to produce an electrical stimulation signal for application to electrodes carried by leads 18, 20.

As mentioned previously, in some embodiments, electrode assemblies 50, 51 may include signal generators (e.g., signal generator 38) such that the electrode assemblies form leadless microstimulators. In this case, electrodes assemblies 50, 51 may include a power source 34 (e.g., a battery) or any other components described with respect to IMD 12 and FIG. 2. For example, one or more electrode assemblies 50, 51 may include a housing, signal generator, and power source. The signal generator and power source may be positioned within the housing. In this manner, electrode assemblies 50, 51 may function as self-contained stimulation devices and take on some or all of the functions of IMD 12. For illustration, however, IMD 12 will generally be described as having leads 18, 20 that electrically couple the IMD to electrode assemblies 50, 51.

Figure 3:
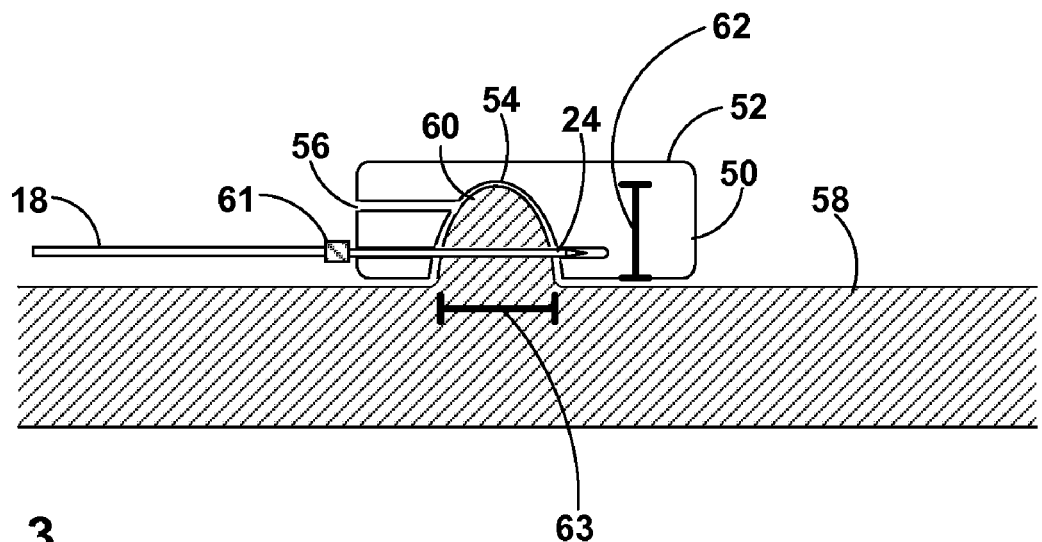
FIG. 3 is a cross-sectional side view that illustrates a distal end of an electrode assembly containing a needle electrode.

FIG. 3 is a cross-sectional side view illustrating a distal end of lead 18 including an electrode assembly 50 containing electrode 24. Electrode assembly 50 includes a housing 52, vacuum cavity 54, and vacuum port 56. Electrode assembly 50 may also include one or more electrodes embedded within housing 52. In some embodiments, electrode assembly 50 may also include a signal generator and a battery within housing 52. In the illustrated embodiment, electrode 24 is attached to wall 58 of stomach 22. More specifically, electrode 24 comprises a needle that extends at least partially through tissue within vacuum cavity 54. In some applications, the tissue may be gastrointestinal tissue, such as tissue associated with the stomach or small intestine of a human patient. In the illustrated embodiment, electrode 24 may also be referred to as needle electrode 24. Needle electrode 24 is advanced to contact at least a portion of the tissue in vacuum cavity 54. In particular, needle electrode 24 may penetrate at least a portion of the tissue. In other embodiments, instead of penetrating tissue with a needle electrode, electrode 24 could be an electrode contact, surface or probe that is placed in contact with tissue.

As will be described in further detail with respect to FIGS. 6A-6C, needle electrode 24 may be moved between a retracted position that allows gastrointestinal tissue to be drawn into vacuum cavity 54 and an extended position in which the needle electrode extends into gastrointestinal tissue within vacuum cavity 54. With further reference to FIG. 3, when needle electrode 24 is in its retracted position, vacuum pressure may be applied to vacuum cavity 54 via vacuum port 56 to draw gastrointestinal tissue into vacuum cavity 54. When needle electrode 24 is in its extended position, the needle electrode may attach electrode assembly 50 to the gastrointestinal tract of patient 16, e.g., stomach wall 58, while at the same time electrically coupling the needle electrode 24 to tissue within the vacuum cavity 54. In some embodiments, electrode assembly 50 may also include one or more anchoring mechanisms 60, such as sutures, hooks, barbs, helical structures, or surgical adhesives, to further secure electrode assembly 50 to the gastrointestinal tract.

At least a portion of needle electrode 24 may comprise any of a variety of electrically conductive, biocompatible materials which are well known in the medical art, such as stainless steel, platinum, platinum-irridium, nickel, nickel-cobalt alloys, or the like. In some embodiments, other portions of needle electrode 24 may be at least partially electrically insulated by insulating layers formed from insulative materials, such as polyurethane, silicone or other materials. Hence, at least a portion of needle electrode 24 may be conductive, e.g., to deliver electrical stimulation to the stomach wall 58 or another location of the gastrointestinal tract. Alternatively, in some embodiments, needle electrode 24 may form a sense electrode to sense physiological electrical signals. In other embodiments, needle electrode 24 may include separate surfaces for sensing and stimulation. Needle electrode 24 may be electrically and mechanically coupled to IMD 12 via lead 18. Needle electrode 24 may be coupled to lead 18 via collar 61 of needle electrode 24. For example, collar 61 of needle electrode 24 may be welded, soldered, bonded or otherwise mechanically and electrically coupled to one or more conductors within lead 18. In some embodiments, multiple conductive portions of needle electrode 24 may be coupled to respective conductors within lead 18 via a through-hole that extends through collar 61.

A depth 62 of vacuum cavity 54 may be configured to access a selected layer of stomach wall 58 or another portion of the gastrointestinal tract. In addition, the height at which the needle electrode 24 is deployed relative to the depth of the vacuum cavity may also be selected to permit deployment at a selected tissue layer. For example, depth 62 of vacuum cavity 54 may be approximately 1 millimeter (mm) to 6 mm. A maximum diameter 63 of vacuum cavity 54 may be approximately 1 mm to 6 mm. For certain therapies and/or patients, stimulation efficacy may be dependent upon which layer of stomach wall 58 is stimulated. Inserting conventional electrodes into stomach wall 58 or other locations of the gastrointestinal tract (e.g., using a needle and forceps) can be very time consuming. Additionally, it is difficult to control insertion depth accuracy and, therefore, access a selected tissue layer with conventional electrodes.

Figure 4:
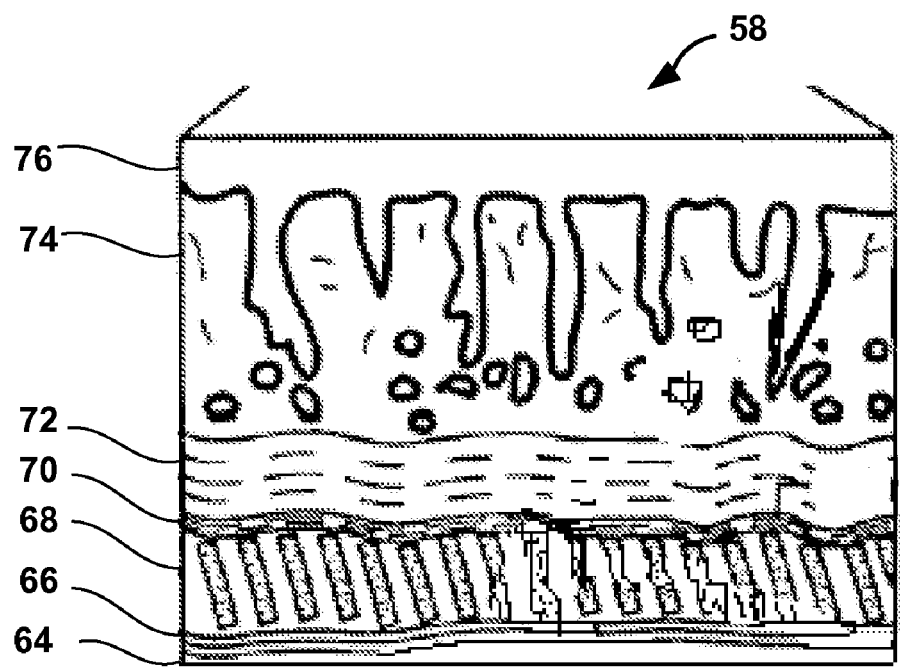
FIG. 4 is a cross-sectional side view that illustrates a segment of a stomach wall.

FIG. 4 is a cross-sectional side view a segment of stomach wall 58. Stomach wall 58 is composed of several layers of tissue including serosa 64, longitudinal muscle layer 66, circular muscle layer 68, oblique muscle layer 70, submucosa 72, and mucosa 74. Mucosa 74 lines lumen 76 of the stomach. In some cases, electrode 24 may be placed within the muscularis of the stomach (e.g., within longitudinal muscle layer 66, circular muscle layer 68, or oblique muscle layer 70) or within the serosal 64, submucosal 72, or mucosal 74 region of the stomach wall 58.

The depth 62 of vacuum cavity 54 may be configured to access a selected layer of stomach wall 58. For example, different electrode assemblies 50 may be manufactured with vacuum cavities of various depths. Alternatively, an electrode assembly 50 may have multiple vacuum cavities of different depths. Depending on the intended therapy and/or patient, a clinician or other trained practitioner may select an electrode assembly 50 with a desirable vacuum cavity 54 depth. Depth 62 of vacuum cavity 54 controls the volume of tissue that may be drawn into the vacuum cavity. The vacuum pressure applied to vacuum cavity 54 may draw gastrointestinal tissue into vacuum cavity 54 to sufficiently fill vacuum cavity 54.

To access different layers at selected depths of a tissue site, the depth and volume of vacuum cavity 54 may be appropriately selected. In addition, the height at which the needle electrode 24 is deployed relative to the depth of the vacuum cavity may also be selected to permit deployment at a selected tissue layer. To access different layers of the stomach wall 58, for example, a vacuum cavity 54 may have depths in the range of approximately 1 to 6 mm measured from a surface of the electrode assembly 50 contacting the surface of the stomach wall to a maximum height of the vacuum cavity 54.

To access particular layers in the stomach wall 58, vacuum cavity 54 may have various depths, diameters, and volumes. For example in some embodiments, vacuum cavity 54 may have one of the following dimensions: a maximum diameter of approximately 1 mm, height of approximately 1 mm, and volume of approximately 0.5 cubic mm; a maximum diameter of approximately 2 mm, height of approximately 2 mm, and volume of approximately 3.5 cubic mm; a maximum diameter of approximately 3 mm, height of approximately 3 mm, and volume of approximately 12 cubic mm; a maximum diameter of approximately 4 mm, height of approximately 4 mm, and volume of approximately 25 cubic mm; a maximum diameter of approximately 5 mm, height of approximately 5 mm, and volume of approximately 50 cubic mm; or a maximum diameter of approximately 6 mm, height of approximately 6 mm, and volume of approximately 85 cubic mm. In general, needle electrode 24 may have a length of approximately 1 to 10 mm, and an average diameter of approximately 0.5 to 2.0 mm, assuming a substantially circular cross-section of needle electrode 24. In some embodiments, needle electrode 24 may have a non-circular cross-section. Also, needle electrode 24 may have a tapered profile such that the distal end of the needle electrode 24 that penetrates a tissue site, such as the stomach wall, tapers to a sharp, pointed tip.

Figure 5A:
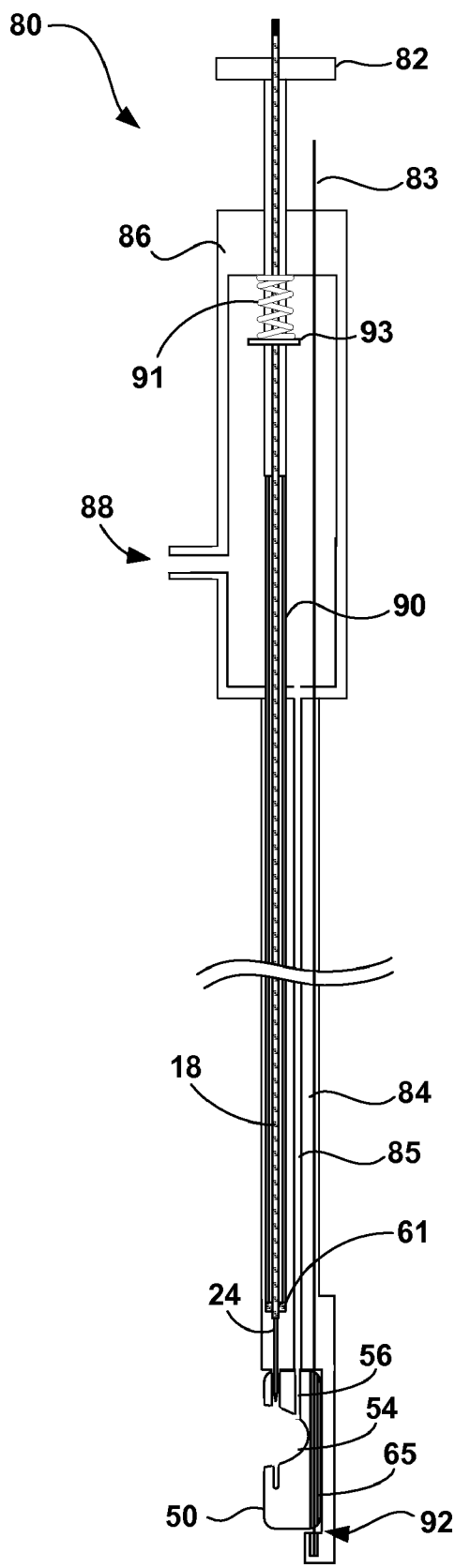
FIGS. 5A and 5B are a cross-sectional side view and a bottom view, respectively, that illustrate a delivery instrument that may be used to implant an electrode assembly within a stomach wall.
Figure 5B:
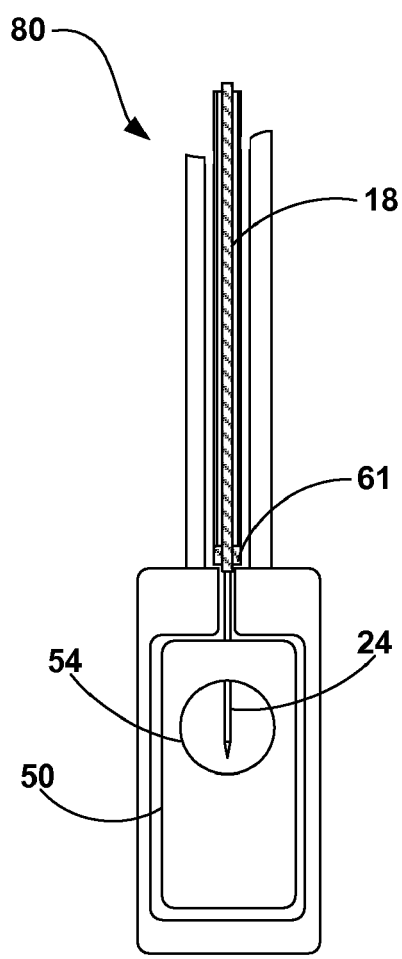

A delivery instrument may be used to position electrode assembly 50 and apply the vacuum pressure to vacuum cavity 54. FIGS. 5A and 5B illustrate an example of a delivery instrument 80, which may also be referred to as a deployment device, that may be used to deploy electrode assembly 50 adjacent stomach wall 56. FIG. 5A is a cross-sectional side view of delivery instrument 80, and FIG. 5B illustrates a bottom plan view of delivery instrument 80. As described herein, delivery instrument 80 applies a vacuum pressure to stomach wall 56 to draw gastrointestinal tissue into vacuum cavity 54. Delivery instrument 80 then advances needle electrode 24 into the gastrointestinal tissue drawn into vacuum cavity 54. A vacuum source (not shown) is coupled to a proximal end of delivery instrument 80 and controls delivery of the vacuum pressure to delivery instrument 80. Delivery instrument 80 may include tubular member 84 for conveying the vacuum pressure through delivery instrument 80 to vacuum cavity 54.

Delivery instrument 80 may be sized to fit within stomach 22 of patient 16 and may be flexible or curved to conform to a shape of stomach 22 at the target region. Delivery instrument 80 includes a proximal portion having a handle 86 and a flexible tubular member 84 that extends from handle 86 to a distal end of delivery instrument 80. Electrode assembly 50 is coupled to a distal end of delivery instrument 80 for implantation at a particular location of stomach 22. The distal end of delivery instrument 80 includes a chamber 92 sized to hold electrode assembly 50.

Delivery instrument 80 may include locking wire 83 that may be employed to retain electrode assembly 50 at the distal end of delivery instrument 80. Delivery instrument 80 may include a locking lumen (not shown) to accommodate locking wire 83. When electrode assembly 50 is coupled to the distal end of delivery instrument 80, the locking lumen of delivery instrument 80 may align with a locking lumen 65 of electrode assembly 50 which removably carries locking wire 83. Locking wire 83 may extend through the locking lumen of delivery instrument 80 and locking lumen 65 of electrode assembly 50 to retain the electrode assembly during deployment. Locking wire 83 may be retracted at the proximal end of delivery instrument 80 following attachment of electrode assembly 50 to stomach wall 58, causing electrode assembly 50 to become disengaged from delivery instrument 80. At this point, once delivery instrument 80 is withdrawn, electrode assembly 50 remains in place at the captured tissue site. In some cases, locking wire 83 and associated locking channels may be constructed in a manner similar to locking wires used for deployment of a monitoring probe as described in U.S. Pat. No. 6,689,056 to Kilcoyne et al.

Delivery instrument 80 includes a vacuum inlet 88 on handle 86 to couple delivery instrument 80 to a vacuum source (not shown). A vacuum line 85 may be provided to extend along the length of tubular member 84 within delivery instrument 80 provide an interface between delivery instrument 80 and vacuum port 56 of electrode assembly 50, and thereby apply the suction from the vacuum source to stomach wall 58 in order to draw tissue into vacuum cavity 54 of electrode assembly 50.

Upon drawing tissue of stomach 22 into vacuum cavity 54, delivery instrument 80 may affix electrode assembly 50 to the tissue. In some embodiments, delivery instrument may include a sheath 90 that at least partially surrounds lead 18 and a spring mechanism 91. Sheath 90 may be generally rigid or at least have sufficient column strength to permit it to serve as a push rod element to drive needle electrode 24 into tissue capture in vacuum cavity 54. Accordingly, sheath 90 may be constructed of any of a variety of relatively rigid materials such as metals or plastics. Sheath 90 may be laterally flexible but exhibit sufficient rigidity to provide column strength to support a longitudinal pushing action against needle electrode 24. A distal end of sheath 90 may bear against collar 61 of needle electrode 24. Spring mechanism 91 may be actuated to advance sheath 90 toward vacuum cavity 54 such that spring mechanism 91 forces sheath 90 to bear against collar 61 and advances needle electrode 24 through the tissue within vacuum cavity 54 in order to anchor electrode assembly 50 to the gastrointestinal tract. In this manner, needle electrode 24 is advanced from a retracted position in which it does not extend substantially into vacuum cavity 54, thereby allowing tissue to be drawn into vacuum cavity 54, to an extended position in which it penetrates such tissue captured within vacuum cavity 54.

As illustrated in FIGS. 5A and 5B, spring mechanism 91, sheath 90, lead 18, needle electrode 24, and collar 61 may be generally coaxial. In particular, lead 18 is coupled to collar 61 and needle electrode 24, and resides within an inner lumen of sheath 90. Spring mechanism 91 bears against a collar 93 forming a proximal end of sheath 90, to drive sheath 90 axially along the length of tubular member 84. Spring mechanism 91 may be initially biased in a compressed position and then released to extend from the compressed position to an expanded position, thereby driving sheath 90.

Any of a variety of release mechanisms may be provided such as a cam or lever arrangement that permit retention of spring mechanism 91 in its compressed position and then selective release of the spring mechanism. Although spring mechanism 91 is illustrated for purposes of example, any other appropriate means of advancing needle electrode 24 may be used. For example, a plunger 82 may be manually actuated into handle 86 in order to advance sheath 90 and cause needle electrode 24 to advance through the tissue drawn into vacuum cavity 54. Once needle electrode 24 is advanced through the gastrointestinal tissue within vacuum cavity 54, electrode assembly 50 detaches from delivery instrument 80, along with lead 18.

Notably, the coaxial arrangement of lead 18 within sheath 90 permits the lead 18 to be readily withdrawn from delivery instrument 80 once needle electrode 24 penetrates the tissue in vacuum cavity 54. In some embodiments, plunger 82 may include a shaft that further defines a lumen to receive lead 18. Lead 18 may extend outside of delivery instrument 80 and may include one or more proximal electrical contacts for connection to one or more terminals in IMD 12. The one or more contacts may be electrically coupled to needle electrode 24 via one or more internal conductors within lead 18.

Figure 5C:
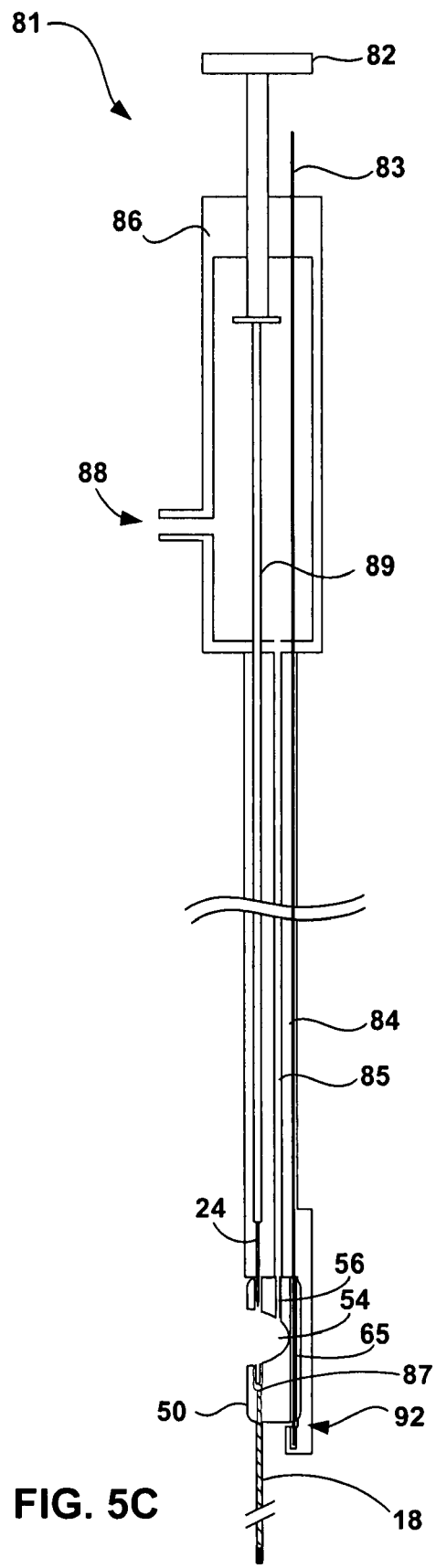
FIG. 5C is a cross-sectional side view of the delivery instrument illustrated in FIG. 5A with an alternative needle deployment and lead mechanism.

FIG. 5C is a cross-sectional side view of an alternative delivery device 81 that may be used to deploy an electrode assembly 50. Delivery instrument 81 is similar to delivery instrument 80 but includes a modified needle deployment mechanism and lead. Delivery device 81 has many of the features and characteristics of delivery instrument 80 including plunger 82, locking wire 83, tubular member 84, vacuum line 85, handle 86, vacuum inlet 88, and chamber 92. However, delivery device 81 utilizes stylet 89 rather than sheath 90.

Stylet 89 may be advanced, e.g., via plunger 82, to push needle electrode 24 into vacuum cavity 54. In the illustrated embodiment, electrode assembly 50 includes electrical contact 87 that passes out of the housing of electrode assembly 50 and is coupled to lead 18, which in turn connects to a medical device, e.g., a stimulation device. Hence, lead 18 extends out of a distal end of electrode assembly 50 rather than a proximal end. If desired, lead 18 may be temporarily bent around the distal end of chamber 92 and pulled back toward the proximal end of delivery device 81 during deployment of the delivery device so that it does not interfere with movement of the delivery device 81 in a distal direction toward the desired tissue site. Then, following attachment of electrode assembly 50 to the tissue site, the electrode assembly 50 may be detached from delivery device 81, and a proximal end of lead 18 (i.e., an end away from the interconnection with needle electrode 24) may be routed, tunneled or otherwise directed to an appropriate location for interconnection with an IMD.

In other embodiments, electrical contact 87 may be mechanically and electrically coupled to stimulation circuitry within electrode assembly 50. When stylet 89 advances needle electrode 24, needle electrode 24 may make mechanical and electrical contact with electrical contact 87. In some embodiments, including a lead 18 or otherwise, electrical contact 87 may include a spring loaded mechanism or any other appropriate contractible/expandable mechanism to ensure sufficient electrical coupling pressure between the distal end of needle electrode 24 and electrical contact 87. Electrical contact 87 may be coupled to lead 18 via any of a variety of techniques such as soldering, welding, crimping, or the like. After needle electrode 24 has been deployed, stylet 89 and locking wire 83 may be withdrawn so that delivery instrument 89 may be detached from electrode assembly 50.

Figure 5D:
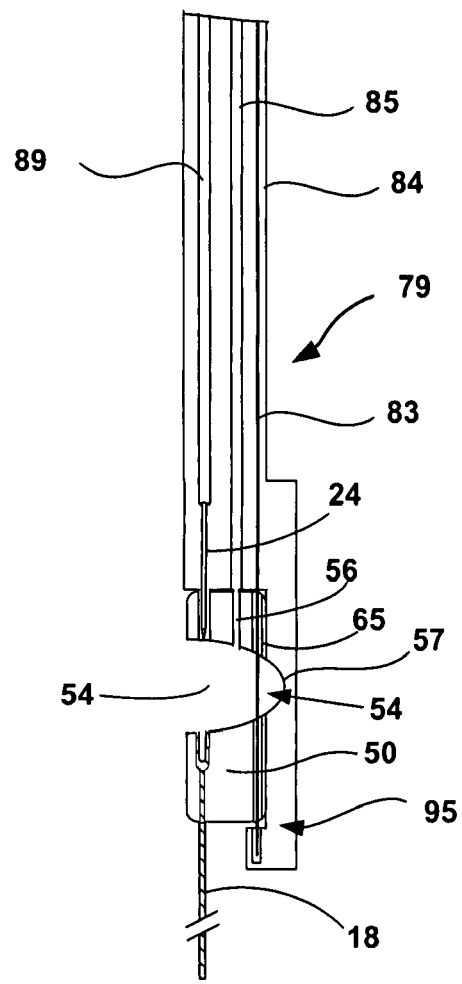
FIG. 5D is a cross-sectional side view of a distal end of the delivery instrument illustrated in FIG. 5C with an alternative chamber to hold an electrode assembly.

FIG. 5D is a cross-sectional side view of a distal end of another alternative delivery instrument 79. Delivery instrument 79 is similar to delivery instrument 81 but includes a modified chamber 95 to hold electrode assembly 50. In the embodiment illustrated in FIG. 5D, vacuum cavity 54 extends through electrode assembly 50 and into chamber 95 of delivery instrument 79, such that electrode assembly 50 defines a hole in a top surface. The hole aligns with a cavity defined in chamber 95 such that vacuum cavity 54, in effect, extends through electrode assembly 50 and into chamber 95. Locking wire 83 extends through attachment cavity 54 and holds electrode assembly 50 together until needle electrode 24 is deployed.

When vacuum pressure is applied to vacuum cavity 54, some tissue will extend past the surface of electrode assembly 50 and into a recessed cavity 57 within chamber 95 of delivery instrument 70. Stylet 89 may be advanced to push needle electrode 24 into tissue within vacuum cavity 54. After needle electrode 24 is deployed, locking wire 83 and stylet 89 may be retracted to permit delivery instrument 79 to be removed from electrode assembly 50.

If a needle electrode is to be implanted deep into a tissue, including the entire depth of the vacuum cavity within the electrode assembly may substantially increase the size of the electrode assembly. By allowing a chamber 95 of delivery instrument 81 to form a portion of the vacuum cavity, as illustrated in FIG. 5D, the depth of the attachment cavity may be increased without increasing the depth of the electrode assembly. In some embodiments, multiple delivery instruments with different chamber configurations may be provided for various applications. In addition, in some embodiments, electrode assembly 50 may include multiple vacuum cavities of different depths to capture different, selected tissue layers, where at least one of the vacuum cavities is combined with the recessed cavity 57 in chamber 95 to form a larger, deeper cavity to access deeper tissue layers.

Figure 5E:
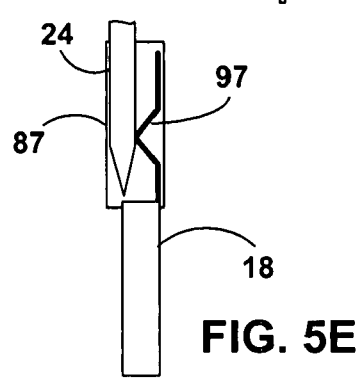
FIG. 5E is an enlarged view of an example spring contact for electrical interconnection of a needle electrode and a lead.

FIG. 5E is an enlarged view of an example spring contact for electrical interconnection of a needle electrode 24 and a lead 18. As shown in FIG. 5E, electrical contact 87 may include a cylindrical channel to receive needle electrode 24. A leaf spring contact 97 may be provided within the cylindrical channel to provide spring-biased electrical contact between needle electrode 24 and one or more electrical conductors within lead 18. If needle electrode 24 includes multiple electrical contacts, multiple leaf spring contacts may be provided to couple the contacts to respective electrical conductors within lead 18. Lead 18 may have conductors directly coupled to leaf spring contact. Alternatively, electrical contact 87 may further include a small terminal block to manage interconnections between one or more leaf spring contacts and one or more electrical conductors.

Figure 6C:
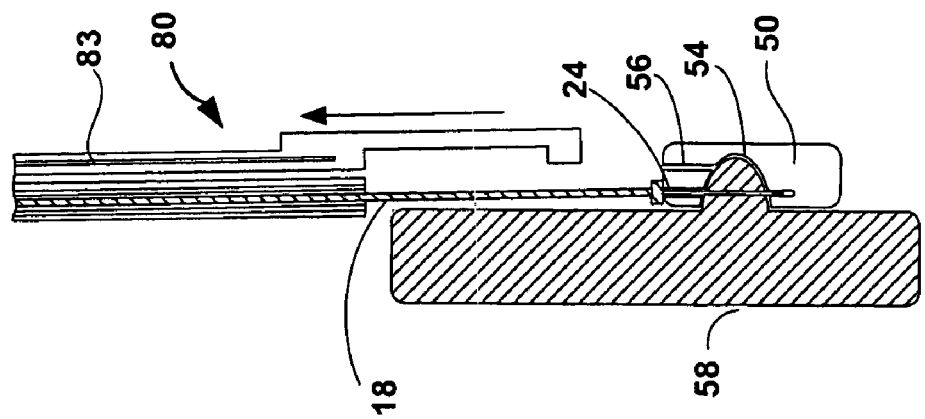
FIGS. 6A-6C are cross-sectional side views of one embodiment of a distal end of a delivery instrument in operation to affix an electrode assembly to a stomach wall.
Figure 6B:
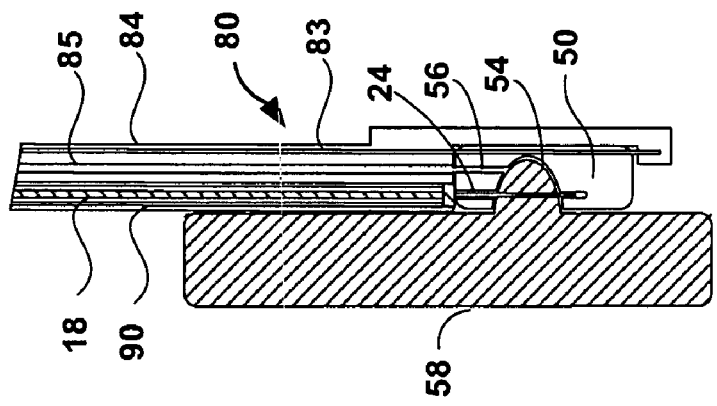
Figure 6A:
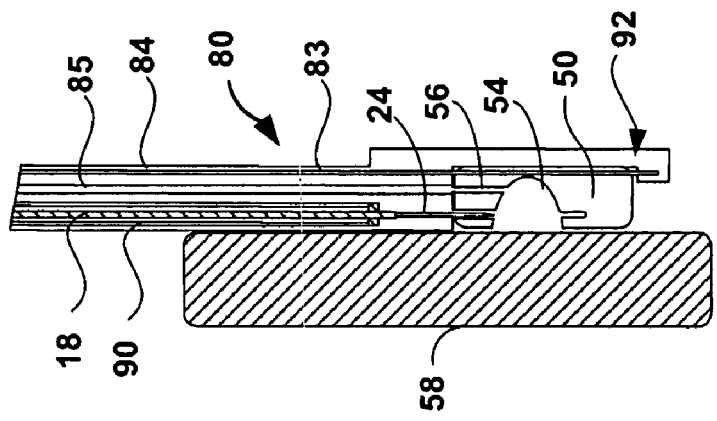

FIGS. 6A-6C are cross-sectional side views of one embodiment of a distal end of a delivery instrument 80 at various stages of operation to affix electrode assembly 50 to stomach wall 58. FIG. 6A illustrates a distal end of delivery instrument 80 positioned proximal to stomach wall 58. In the illustrated embodiment, the distal end of delivery instrument 80 includes a chamber 92 sized to hold electrode assembly 50. Chamber 92 may hold electrode assembly 50 in place by interconnection of lead 18 with needle electrode 24, vacuum pressure from vacuum line 85, and/or frictional engagement between chamber 92 and the outer surface of electrode assembly 50, or other mechanisms. In the illustrated embodiment, locking wire 83 extends through delivery instrument 80 and electrode assembly 50 to aid in holding electrode assembly 50 in place.

Tubular member 84 provides a line 85 for conveying a vacuum pressure created by a vacuum source (not shown) to vacuum cavity 54. As a result, delivery instrument 80 draws a portion of the stomach wall 58 into vacuum cavity 54 of electrode assembly 50, as shown in FIG. 6B. FIG. 6B also illustrates anchoring of electrode assembly 50 to stomach wall 58 via advancement of needle electrode 24 by sheath 90 through the tissue drawn into cavity 54 of electrode assembly 50. During this process, the vacuum pressure maintains the suction that draws tissue into vacuum cavity 54 to stabilize the tissue and ensure stable electrical contact between needle electrode 24 and the tissue.

FIG. 6C illustrates the detachment of electrode assembly 50 from delivery instrument 80. Locking wire 83 is retracted from electrode assembly 50 to allow electrode assembly 50 to become disengaged from delivery instrument 80. During deployment, locking wire 83 may extend axially through a channel in delivery instrument 80 and a channel in electrode assembly 50 to retain electrode assembly within delivery instrument 80. The distal end of locking wire 83 may reside within a distal recess in delivery instrument 80. Upon axial withdrawal in a proximal direction, the locking wire 83 is removed from electrode assembly 50, permitting the electrode assembly 50 to be released from delivery instrument 80.

As illustrated in FIG. 6C, lead 18 remains coupled to electrode assembly 50 and disposed within delivery instrument 80. Delivery instrument 80 is withdrawn from the patient, and lead 18 is then removed from the delivery instrument and utilized in the desired manner, e.g., to sense electrical activity and/or deliver electrical stimulation to stomach wall 58. For example, deployment instrument 80 may be pulled in a proximal direction away from electrode assembly 50, in which case lead 18 slides out of the deployment device and remains coupled to needle electrode 24. Lead 18 then may be guided or tunneled to IMD 12, which may also be implanted within the patient.

Electrode assembly 50 may be implanted on an exterior or interior portion of the gastrointestinal tract. For example, electrode assembly 50 may be laproscopically or surgically implanted proximate to an exterior surface of the gastrointestinal tract. In other embodiments, electrode assembly 50 may be affixed proximate to an interior surface of the gastrointestinal tract, e.g., via endoscopic delivery.

In laparoscopic surgery, patient 16 receives general anesthesia and one or more small incisions are made in an abdomen of patient 16, usually via a trocar or other surgical instrument. Delivery instrument 80 may be inserted into an abdomen of patient through the one or more incisions. Once inserted, delivery instrument 80 may be positioned to place electrode assembly 50 proximate to an exterior surface of a gastrointestinal wall. Electrode assembly 50 may be deployed as described with respect to FIGS. 6A-6C.

Electrode assembly 50 may be deployed on an outer surface of a tissue site, such as stomach 22. In this case, delivery instrument 80 may be introduced into patient 16 through open surgery or laparoscopic surgical techniques. In other cases, electrode assembly 50 may be placed intra-luminally within a body lumen, such as the esophagus, stomach, intestines or other body lumens. For example, if electrode assembly 50 is a self-contained, leadless stimulator, then delivery instrument 80 could be introduced orally or nasally into the esophagus and then into the inner lumen of stomach 22 to place electrode assembly 50 on the inner surface of stomach wall 58. Delivery instrument 80 and electrode assembly 50 may facilitate implantation of the electrode assembly in the interior of the stomach or another body lumen, at a selected depth or tissue layer that is selected as a function of the depth and/or volume of vacuum cavity 54. In this case, delivery instrument 80 may be sized for introduction into the gastrointestinal tract, e.g., via the esophagus 102. A distal end of delivery instrument 80 enters the esophagus, via either the nasal cavity or oral cavity, and extends through esophagus and through the lower esophageal sphincter (LES) to a desired placement location.

As described with respect to FIGS. 6A-6C, vacuum pressure is delivered through delivery instrument 80 to vacuum cavity 54 to draw gastrointestinal tissue on the interior surface of stomach 22 into vacuum cavity 54. Once tissue is fully drawn into vacuum cavity 54, needle electrode 24 may be advanced from its retracted position to its extended position to penetrate the captured tissue. Advancement of needle electrode 24 attaches assembly 50 to the interior of stomach wall

58 and couples the needle electrode to a selected tissue layer at a target location within stomach 22. Delivery instrument 100 is then detached from electrode assembly 50 and removed from patient 16 via the esophagus.

In embodiments in which electrode assembly 50 is deployed within the interior of the gastrointestinal tract, lead 18 may extend through oral cavity 104 or nasal cavity 106 and be coupled to an external electrical stimulator outside of patient 16. In other embodiments, electrode assembly 50 may be leadless (e.g., without lead 18) and include a signal generator and a power source, e.g., within housing 52 of electrode assembly 50, such that electrode assembly 50 functions as a self-contained electrical stimulator. In embodiments in which electrode assembly 50 is deployed within the gastrointestinal tract, electrode assembly 50 may be substantially cylindrical or capsule-shaped with rounded edges to help allow boluses and other food and/or waste matter to easily pass by electrode assembly 50.

FIGS. 7-16 illustrate various embodiments of electrode assemblies. Electrode assemblies 110, 120, and 130 are similar to electrode assembly 50 but include multiple vacuum cavities. Electrode assemblies 50, 110, 120, and 130 are illustrated for purposes of example, and in other embodiments, an electrode assembly may include any number of vacuum cavities. A locking wire 83 may be used, but is not shown in FIGS. 7-16.

Figure 7:
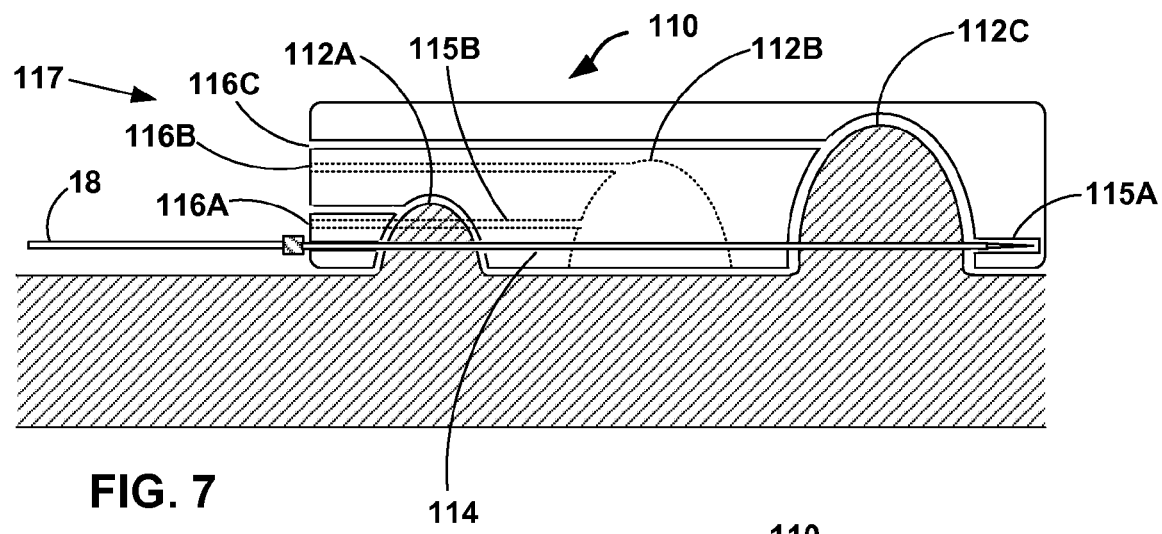
FIG. 7 is a cross-sectional side view of an alternative embodiment of an electrode assembly.
Figure 8:
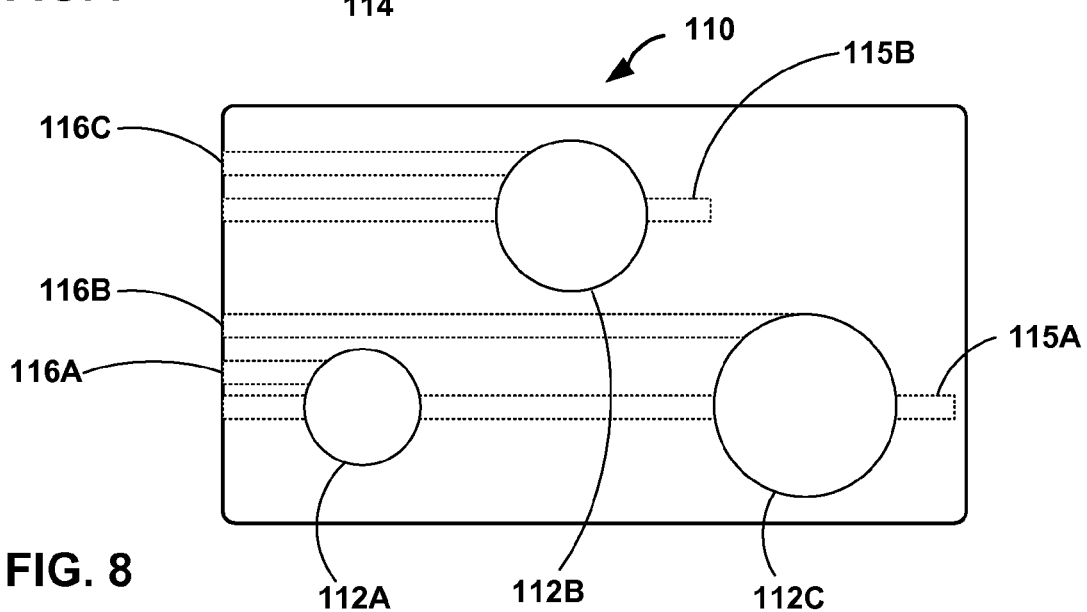
FIG. 8 is a bottom view of the electrode assembly illustrated in FIG. 7.

FIG. 7 is a cross-sectional side view of electrode assembly 110 including vacuum cavities 112A, 112B and 12C (collectively "vacuum cavities 112"). FIG. 8 illustrates a bottom view of electrode assembly 110 illustrated in FIG. 7. As shown in FIG. 7, lead 18 extends outside of electrode assembly 110. The bottom of electrode assembly 110 refers to the surface which ordinarily would face the tissue site of interest during and following implantation. Vacuum cavities 112A and 112C may be axially aligned with one another, while vacuum cavity 112B may be off-axis, and is therefore shown in phantom. Each of vacuum cavities 112 has a depth configured to access a selected layer of the gastrointestinal tract. In the illustrated embodiment, each of vacuum cavities 112 has a unique depth. Providing vacuum cavities with different depths may allow multiple layers of the stomach wall 58 to be stimulated by multiple electrodes, or allow different, single layers to be selectively stimulated with one electrode by selection of one of the vacuum cavities. Although vacuum cavities 112A-112C with different depths are shown in FIG. 7, in other embodiments, two or more vacuum cavities may have the same depth.

In the embodiment illustrated in FIG. 7, one needle electrode 114 is deployed in electrode port 115A and penetrates stomach tissue in both of vacuum cavities 112A and 112C. In this manner, needle electrode 114 penetrates at a first depth or tissue layer of the tissue in vacuum cavity 112A and at a second, different depth or tissue layer in vacuum cavity 112C. Needle electrode 114 may be electrically and mechanically coupled to a signal generator (e.g., within conductors in electrode assembly 110 in the case of a leadless stimulator or via lead 18). Vacuum cavity 112B includes a separate electrode port 115B in which a needle electrode may be deployed.

In some embodiments, one or more of vacuum cavities 112A-112C may not be penetrated by a needle electrode. For example, a clinician may selectively choose which of vacuum cavities 112A-112C to utilize to access one or more desired depths of stomach tissue. As one example, a clinician may choose to deploy needle electrode 114 to penetrate vacuum cavities 112A and 112C and not deploy a needle electrode into electrode port 115B. In other embodiments, a clinician may choose to penetrate all of vacuum cavities 112A-112C to allow stimulation of various tissue depths to be tested for efficacy and/or used for therapy delivery.

Electrode assembly 110 also includes vacuum ports 116A-116C that may be used to provide suction to vacuum cavities 112A-112C, respectively. In other embodiments, two or more of vacuum cavities 112 may share a single vacuum port. In some embodiments, vacuum pressures of different magnitudes may be applied to different vacuum ports. For example, since the depth of vacuum cavity 112A is smaller than the depths of vacuum cavities 112B and 112C, a low strength suction may be sufficient to draw enough tissue into vacuum cavity 112A to fully fill vacuum cavity 112A. A higher strength suction may be necessary to pull enough tissue into vacuum cavities 112B and 112C, since more tissue must be drawn into vacuum cavities 112B and 112C in order to fill these cavities.

Figure 9:
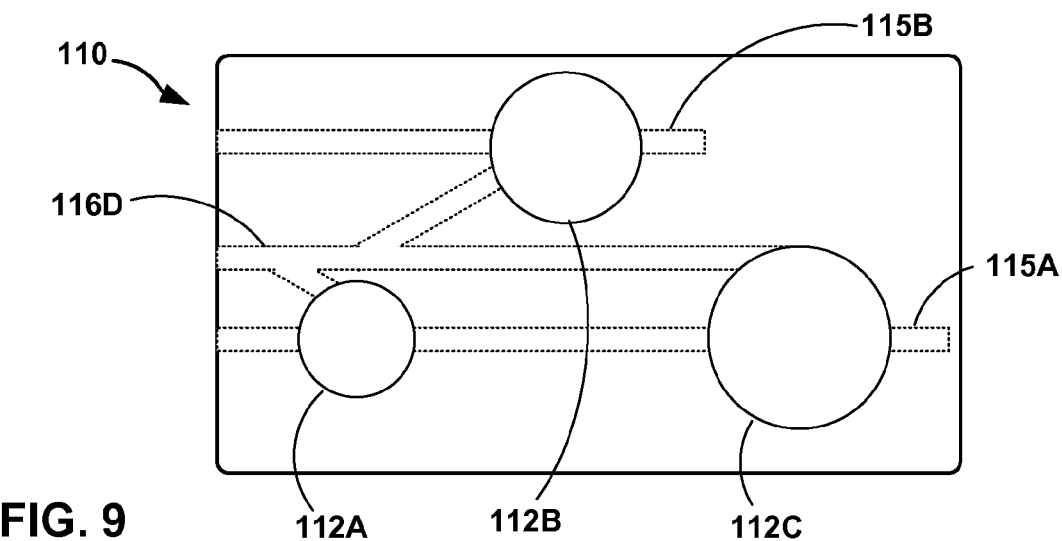
FIG. 9 is a bottom view of electrode assembly illustrated in FIG. 7 with a modified vacuum port arrangement.

FIG. 9 illustrates a bottom view of electrode assembly 110 with a modified vacuum port arrangement. In the embodiment illustrated in FIG. 9, vacuum port 116D may be used to apply suction to each of vacuum cavities 112. As described previously, in other embodiments, each of vacuum cavities 112 may include a separate vacuum port or two or more of vacuum cavities 112 may share a vacuum port.

Figure 10:
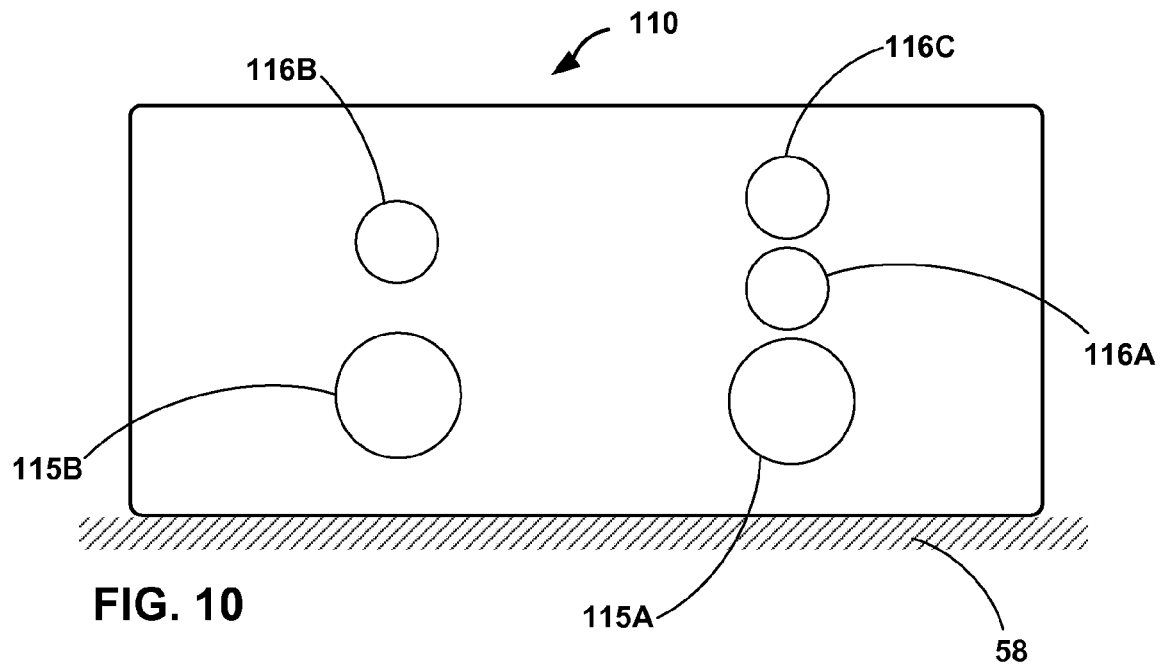
FIG. 10 is an end view of the electrode assembly illustrated in FIG. 7.
Figure 11:
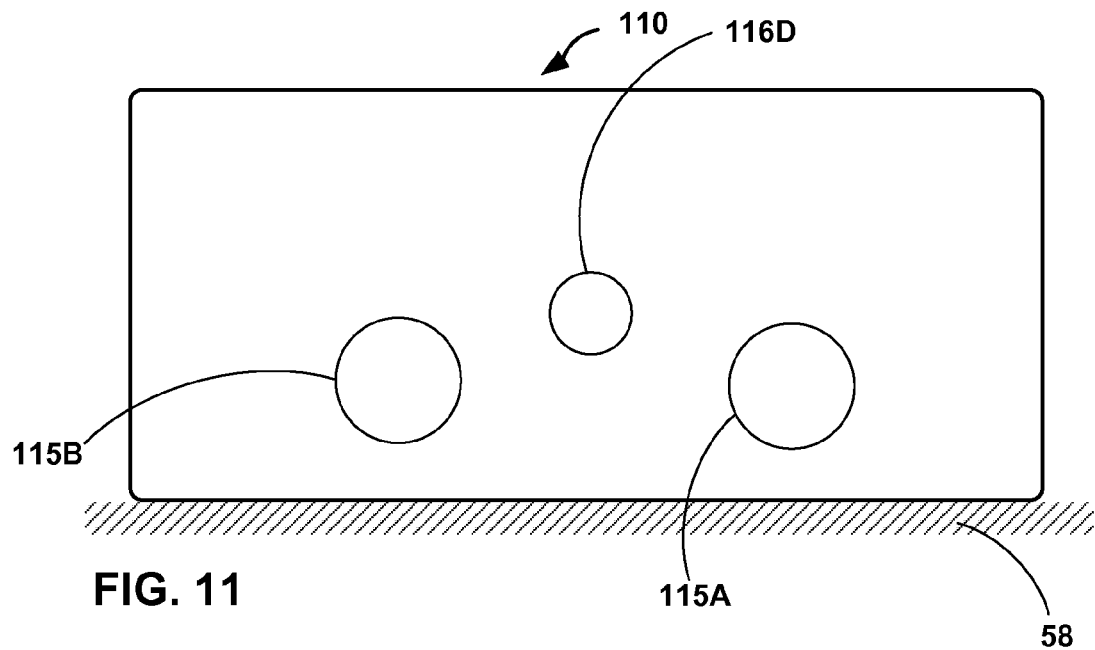
FIG. 11 is an end view of the electrode assembly illustrated in FIG. 9.

FIG. 10 illustrates an end view of electrode assembly 110 including vacuum ports 116A-116C, and FIG. 11 illustrates an end view of electrode assembly 110 including an alternative vacuum port arrangement with one vacuum port 116D, both taken from an end 117 of electrode assembly 110 in FIG. 7. Electrode ports 115A and 115B are shown proximate to stomach wall 58. In the embodiment illustrated in FIG. 10, suction ports 116A-116C are proximate to the deepest portions of vacuum cavities 112 (not shown) to aid in drawing tissue into vacuum cavities 112 to sufficiently fill vacuum cavities 112. In the embodiment illustrated in FIG. 11, vacuum port 116D may be used to apply suction to each of vacuum cavities 112.

Figure 12:
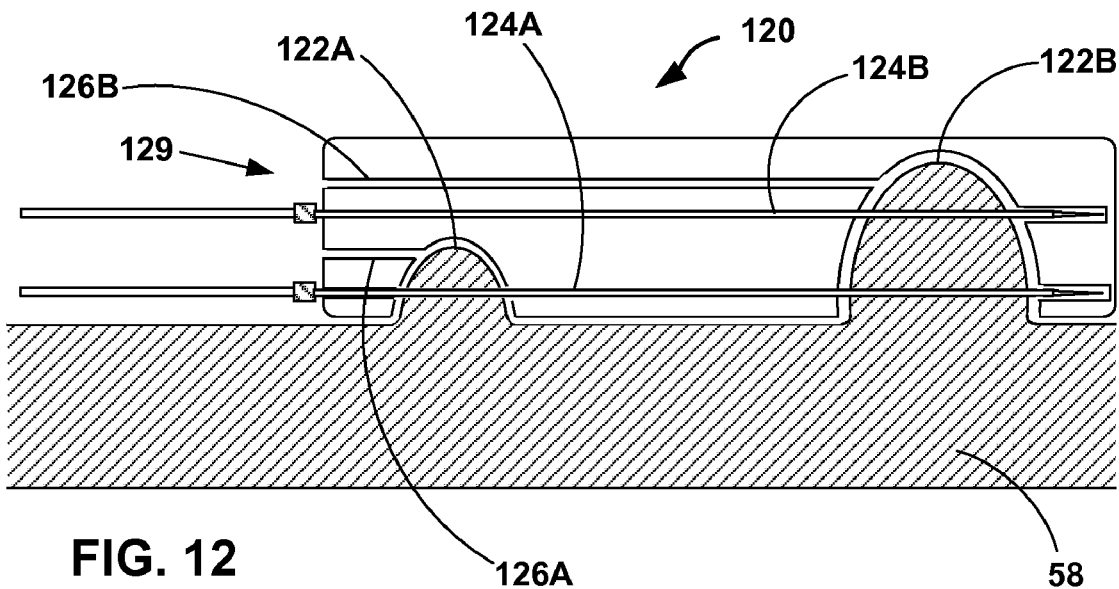
FIG. 12 is a cross-sectional side view of another embodiment of an electrode assembly.

FIG. 12 is a cross-sectional side view of electrode assembly 120 including vacuum cavities 122A and 122B. Each of vacuum cavities 122 has a depth configured to access a selected layer of the gastrointestinal tract. Needle electrode 124A penetrates tissue both within vacuum cavities 122A and 122B, and needle electrode 124B penetrates tissue within vacuum cavity 122B. Multiple needle electrodes may be positioned within one vacuum cavity, for example, to stimulation multiple tissue layers at one position of the gastrointestinal tract. Vacuum pressure may be applied to vacuum cavities 122A and 122B via vacuum ports 126A and 126B, respectively. As described with respect to FIGS. 7 and 8, vacuum pressure of different magnitudes may be applied to different vacuum ports to ensure that tissue is fully drawn into the vacuum cavities. Also, as described with respect to FIG. 7, in some embodiments one of vacuum cavities 122A and 112B may not be penetrated by a needle electrode. In this manner, a clinician may selectively choose which of vacuum cavities 122A and 122B to utilize to access a desired depth of stomach tissue. In other embodiments, one or more needle electrodes may penetrate both of vacuum cavities 122A and 122B.

Figure 13:
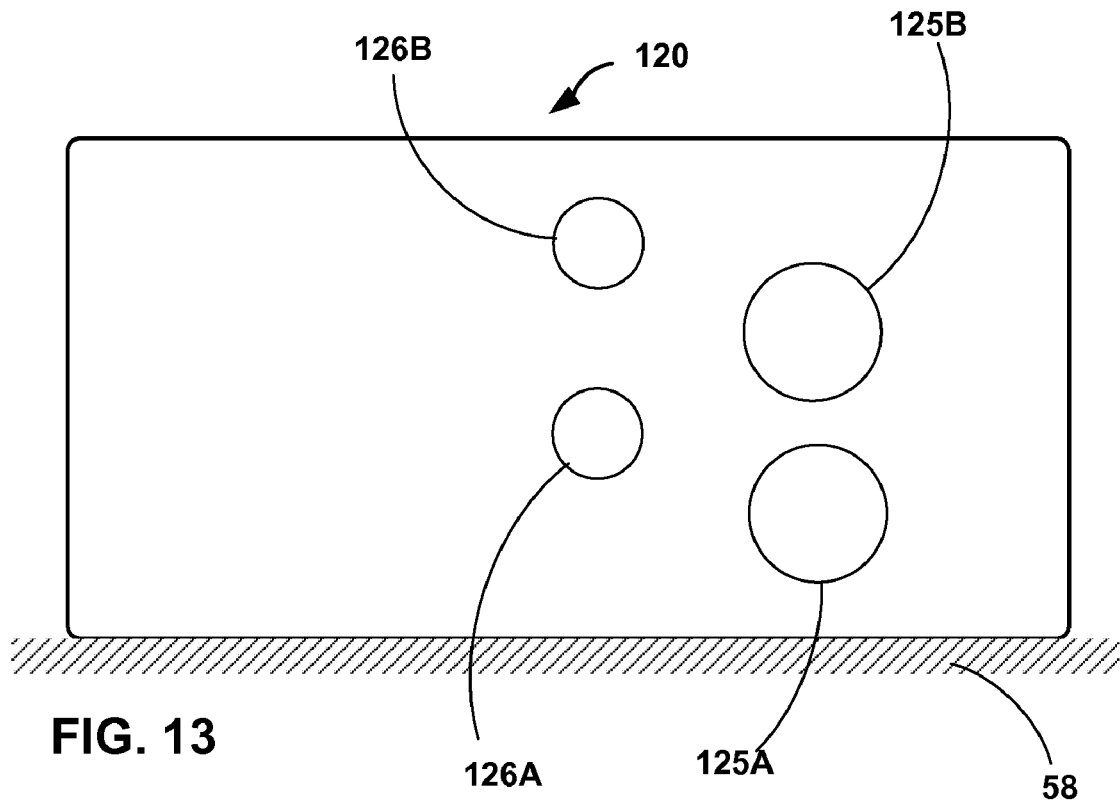
FIG. 13 is an end view of the electrode assembly illustrated in FIG. 12.

FIG. 13 illustrates an end view of electrode assembly 120 illustrated in FIG. 12 from an end 129, shown in FIG. 12. Electrode ports 125A and 125B are located at different distances from stomach wall 58 such that two needle electrodes 124A and 124B can penetrate tissue within vacuum cavity 122B at two different depths. In some embodiments, additional electrode ports may be provided such that two, three or more needles may penetrate tissue at two, three or more depths within vacuum cavity 122B. Suction ports 126A and 126B are positioned to allow suction pressure to be drawn into vacuum cavities 122A and 122B, respectively.

Figure 14:
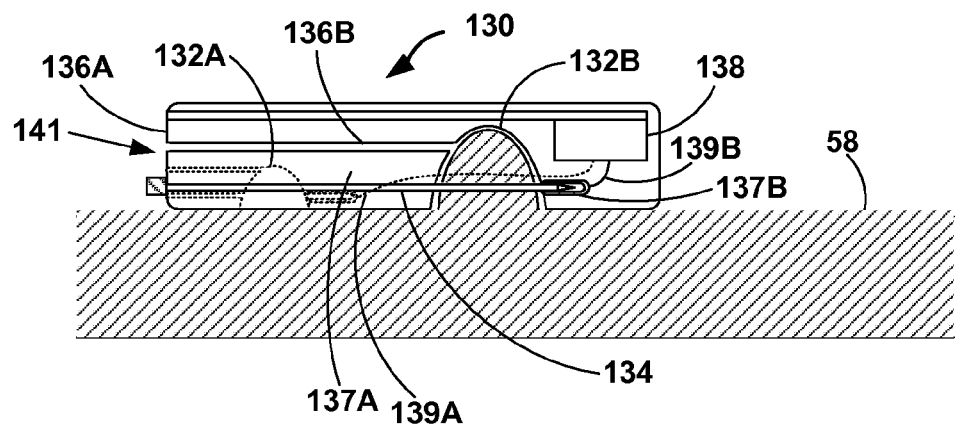
FIG. 14 is a cross-sectional side view of yet another embodiment of an electrode assembly.

FIG. 14 illustrates a cross-sectional side view of electrode assembly 130 including vacuum cavities 132A and 132B. In the illustrated embodiment, vacuum cavities 132A and 132B are different sizes (e.g., have different depths, diameters, and/or volumes). However, in other embodiments, an electrode assembly may include two or more vacuum cavities of substantially similar size, e.g., to access the same tissue layer at two or more locations.

Electrode assembly 130 also includes stimulation circuitry 138, which may include a signal generator (e.g., signal generator 38 of FIG. 2) and/or a power source (e.g., power source 34 of FIG. 2). Electrode assembly 130 also may include a telemetry interface. In embodiments in which electrode assembly 130 includes a signal generator, electrode assembly 130 may function as a self-contained, leadless stimulator.

Electrode assembly 130 includes vacuum cavities 132A and 132B. Needle electrode 134 may be deployed to access tissue within vacuum cavity 132B, and a second needle (not shown) may be deployed to access tissue within vacuum cavity 132A. Vacuum ports 136A and 136B may provide vacuum pressure to vacuum cavities 132A and 132B, respectively. A clinician may selectively choose to utilize one or more needle electrodes to penetrate one or more of vacuum cavities 132A and 132B, for example, to access one or more desired depths of stomach tissue and/or allow stimulation of various tissue depths to be tested for efficacy and/or used for therapy delivery.

Needle 134 may be electrically and mechanically coupled to stimulation circuitry 138. For example, when in its extended position, a distal end of needle 134 may contact electrical contact 137B. Electrical contact 137B may be mechanically and electrically coupled to stimulation circuitry 138 via connector 139B. In some embodiments, electrical contact 137B may include a spring loaded mechanism, such as a leaf spring contact or other spring loaded electrical contact, to ensure substantial mechanical and electrical contact with needle 134. Vacuum cavity 132A may also include an electrical contact 137A and connector 139A to allow a needle extending through vacuum cavity 132A to be electrically and mechanically coupled to stimulation circuitry 138. Needle electrode 134 in cavity 132B and a needle electrode deployed into cavity 132A may form a bipolar electrode pair for delivery of stimulation energy.

Figure 15:
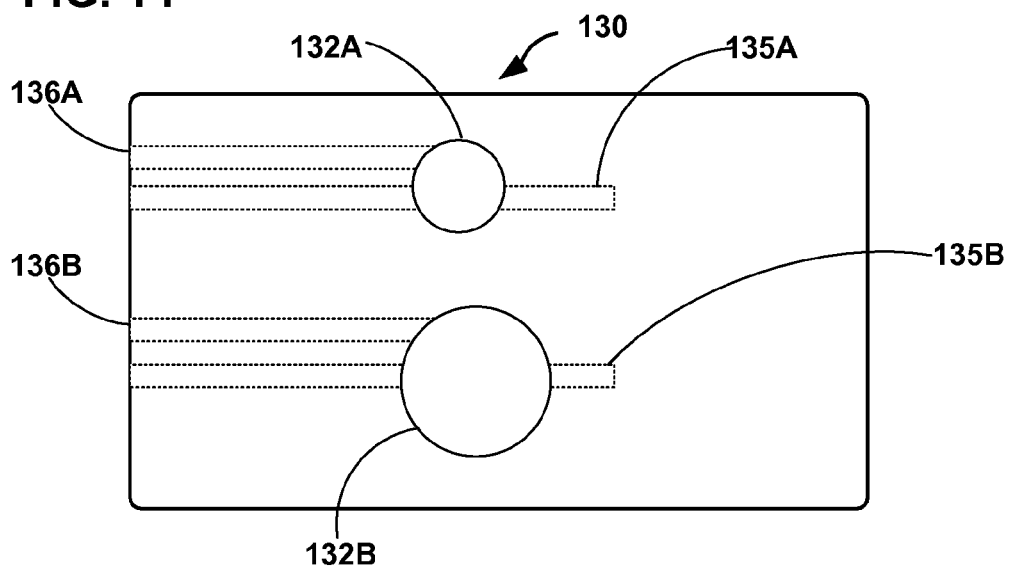
FIG. 15 is a bottom view of the electrode assembly illustrated in FIG. 14.
Figure 16:
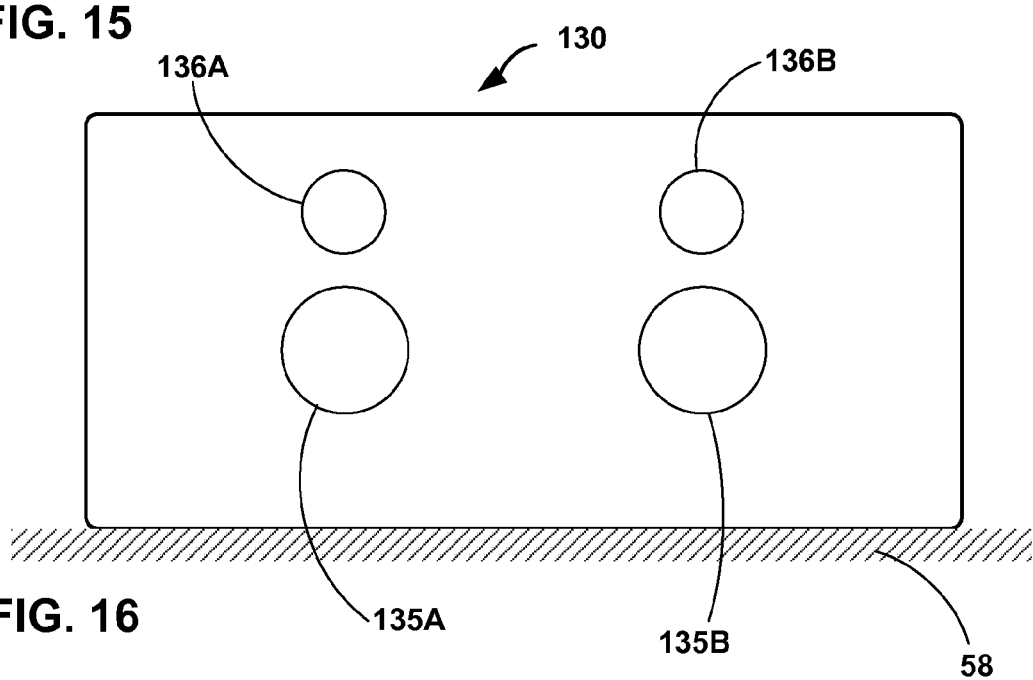
FIG. 16 is an end view of the electrode assembly illustrated in FIG. 14.

FIG. 15 is a bottom view of electrode assembly 130 illustrating vacuum cavities 132A and 132B, electrode ports 135A and 135B, and vacuum ports 136A and 136B in further detail. FIG. 16 is an end view of electrode assembly 130, taken from an end 141 of electrode assembly 130 in FIG. 14. Electrode ports 135A and 135B are located more proximate to stomach wall 58 than vacuum ports 136A and 136B.

Figure 17:
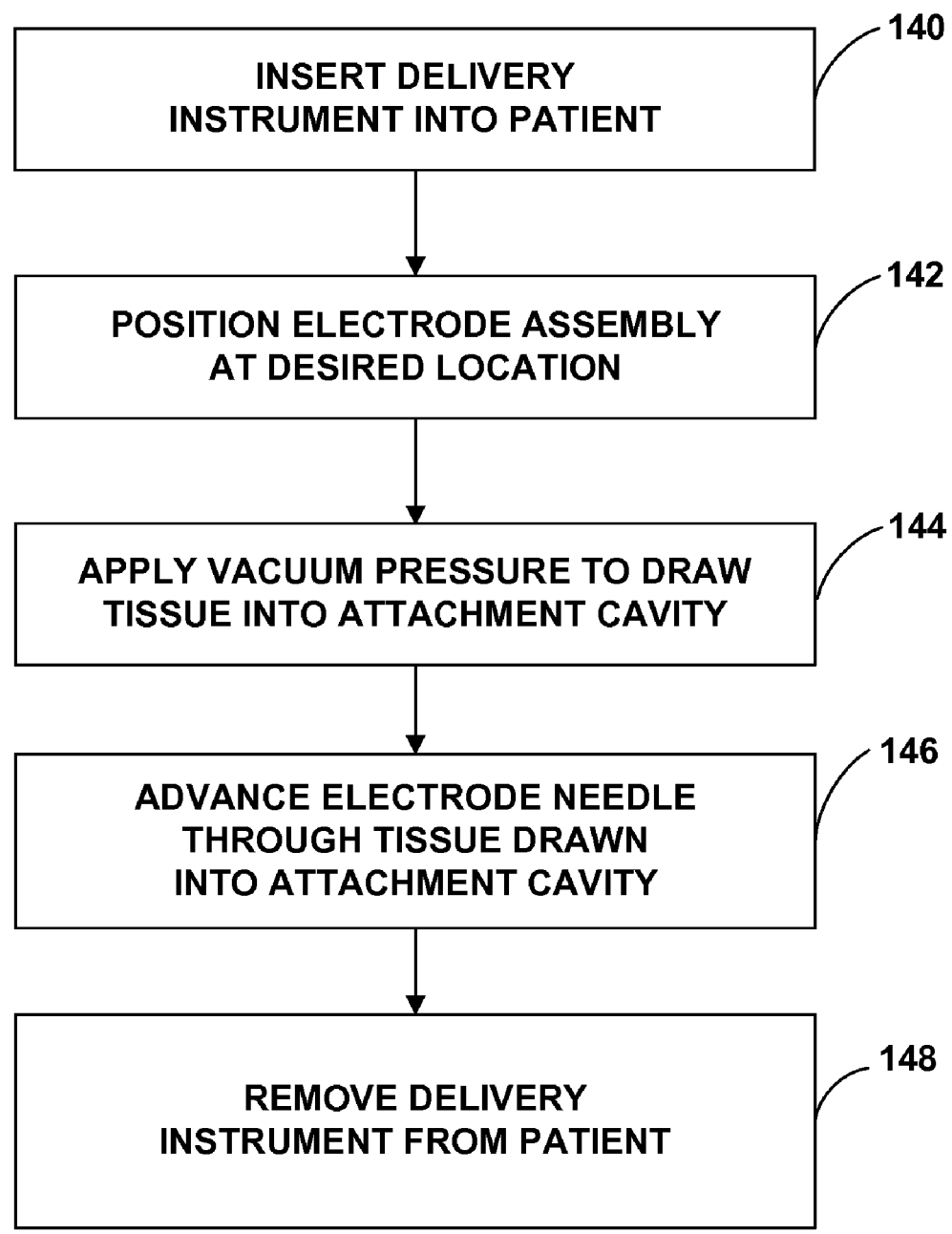
FIG. 17 is a flow diagram illustrating a method of implanting an electrode assembly within the gastrointestinal tract.

FIG. 17 is a flow diagram illustrating a method of implanting an electrode assembly within the gastrointestinal tract. Though the implant procedure is described with respect to electrode assembly 50, this method may be used to implant any electrode assembly (e.g., electrode assembly 110, 120, or 130). Delivery instrument 80, which forms a deployment device, is inserted into patient 16 (140). Electrode assembly 50 may be coupled to a distal end of delivery instrument 80. Electrode assembly 80 is positioned at the desired location of the gastrointestinal tract (142). The implant location may be based on the disorder to be treated and/or the condition of patient 16. A vacuum pressure is applied to stomach wall 58 via delivery instrument 80 and vacuum port 56 to draw gastrointestinal tissue into vacuum cavity 54 (144). After tissue has been drawn into vacuum cavity 54, needle electrode 24 may be advanced through the tissue drawn into vacuum cavity 54 (146), and delivery instrument 80 may be removed from patient 16 (148).

Figure 18A:
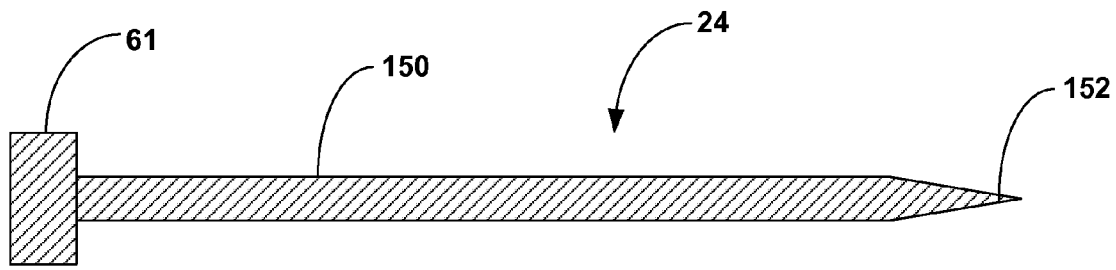
FIGS. 18A, 18B and 18C are side views of example needle electrodes.
Figure 18B:
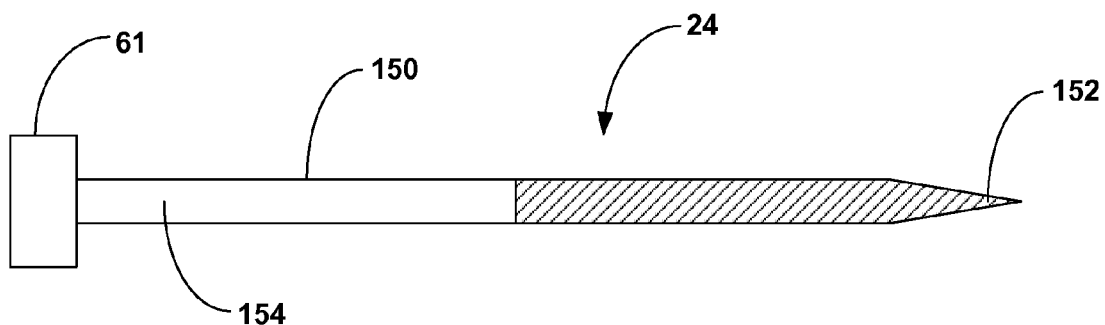
Figure 18C:
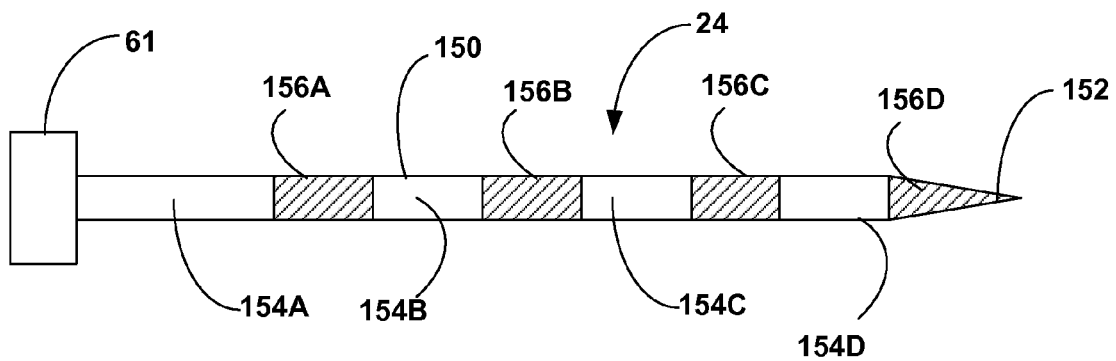

FIGS. 18A, 18B and 18C are side views of example needle electrodes 24 that may be useful in an electrode assembly as described in this disclosure. Each needle electrode 24 in FIGS. 18A-18C may include a collar 61, a shank 150 and a sharp distal tip 152. In the example of FIG. 18A, substantially the entire needle electrode 24 may be formed from an electrically conductive material to form an electrode. Electrical conductors carried by a lead may be electrically coupled directly to collar 61 or to shank 150, e.g., via a through-hole in collar 61, by any of a variety of techniques such as soldering, welding, crimping, or the like.

In the example of FIG. 18B, part of the needle electrode 24 may be covered by an electrically insulative material, such as polyurethane or silicone. For example, a distal portion of shank 150 and tip 152 may be exposed, while the remainder of the shank and collar 61 are covered by the insulative material. In some embodiments, distal tip 152 may be covered by an electrical insulative and/or lubricious material, such as PTFE, to add penetration of needle electrode 24 into tissue captured within a vacuum cavity.

In the example of FIG. 18C, needle electrode 24 includes various sections of electrically insulative material 154A-D that define various electrode regions 156A-156D. In some embodiments, distal tip 152 may extend through and beyond the captured tissue. In other embodiments, distal tip 152 may reside within the capture tissue. In either case, the insulative material in sections 154A-154D may define multiple electrode regions.

If shank 150 has a unitary construction, electrode regions 156A-156D may carry the same electrode potentials. In some embodiments, however, shank 150 may be constructed of separate electrode regions 156A-156D and separate insulative sections 154A-154D. The separate electrode regions 156A-156D may be electrically and mechanically coupled to separate electrical conductors associated with lead 18, thereby producing a multi-electrode needle 24 that permits different electrodes and electrode combinations to be selectively activated and used for sensing and/or stimulation. In the examples of FIGS. 18A-18C, needle electrode 24 may be considered a single electrode or a set of multiple electrodes deployed on a needle-like element.

Various embodiments of the invention have been described. Variations may be made without departing from the spirit and scope of the invention, as broadly embodied herein. These and other embodiments are within the scope of the following claims.

The invention claimed is:

1. An implantable medical device comprising:
    a device housing defining a vacuum cavity and a vacuum port for application of vacuum pressure to draw tissue into the vacuum cavity;
    an electrode that is movable into the vacuum cavity of the device housing to contact at least a portion of the tissue drawn into the vacuum cavity; and
    a lead comprising at least one conductor coupled to the electrode, wherein the lead extends outside the device housing.

2. The device of claim 1, wherein the electrode comprises a needle electrode that is movable into the vacuum cavity to penetrate at least a portion of the tissue drawn into the vacuum cavity.

3. The device of claim 2, further comprising an electrical stimulator electrically coupled to the needle electrode via the lead to deliver electrical stimulation to the tissue.

4. The device of claim 2, wherein a depth of the vacuum cavity is selected to permit deployment of the needle electrode at a selected layer of the tissue.

5. The device of claim 1, wherein the vacuum cavity comprises a first vacuum cavity, and wherein the housing further comprises a second vacuum cavity, and wherein the electrode comprises a needle electrode that is movable to penetrate tissue in at least one of the first and second vacuum cavities.

6. The device of claim 5, wherein the first and second vacuum cavities have different depths, and wherein the different depths are selected to permit deployment of the needle electrode at different, selected layers of the tissue.

7. The implantable medical device of claim 1, wherein the vacuum cavity comprises a first vacuum cavity that defines a first depth, wherein the housing further defines a second vacuum cavity that defines a second depth and a third vacuum cavity that defines a third depth, wherein the first, second and third depths are different from one another, and wherein the electrode comprises a needle electrode that is movable to penetrate tissue in at least one of the first, second and third vacuum cavities.

8. A system comprising:
an electrode assembly comprising:
a housing defining a vacuum cavity and a vacuum port for application of vacuum pressure to draw tissue into the vacuum cavity, and
an electrode that is movable into the vacuum cavity of the housing to contact at least a portion of the tissue drawn into the vacuum cavity;
an electrical stimulator located outside of the housing of the electrode assembly; and
a lead comprising at least one conductor that extends outside the housing of the electrode assembly and electrically couples the electrical stimulator to the electrode.

9. The system of claim 8, wherein the electrode comprises a needle electrode that is movable into the vacuum cavity to penetrate at least a portion of the tissue drawn into the vacuum cavity.

10. The system of claim 9, wherein the lead and the electrical stimulator are fully implantable.

11. The system of claim 9, wherein a depth of the vacuum cavity is selected to permit deployment of the needle electrode at a selected layer of the tissue.

12. The system of claim 8, wherein the vacuum cavity comprises a first vacuum cavity, wherein the housing further comprises a second vacuum cavity, and wherein the electrode comprises a needle electrode that is movable to penetrate tissue in at least one of the first and second vacuum cavities.

13. The system of claim 12, wherein the first and second vacuum cavities have different depths, and wherein the different depths are selected to permit deployment of the needle electrode at different, selected layers of the tissue.

14. The system of claim 8, wherein the vacuum cavity comprises a first vacuum cavity that defines a first depth, wherein the housing further defines a second vacuum cavity that defines a second depth and a third vacuum cavity that defines a third depth, wherein the first, second and third depths are different from one another, and wherein the electrode comprises a needle electrode that is movable to penetrate tissue in at least one of the first, second and third vacuum cavities.

15. A method comprising:
applying vacuum pressure to a vacuum cavity in an electrode assembly housing to draw tissue into the vacuum cavity;
advancing an electrode that is movable into the vacuum cavity of the housing to contact at least a portion of the tissue drawn into the vacuum cavity, wherein the electrode is coupled to at least one conductor in a lead that extends outside the electrode assembly housing, and wherein the lead is coupled to an electrical stimulator that is located outside of the electrode assembly housing; and
delivering electrical stimulation from the electrical stimulator to the tissue via the lead and the electrode.

16. The method of claim 15, wherein the electrode comprises a needle electrode, and advancing comprises advancing the needle electrode into the vacuum cavity to penetrate at least a portion of the tissue drawn into the vacuum cavity.

17. The method of claim 16, wherein a depth of the vacuum cavity is selected to permit deployment of the needle electrode at a selected layer of the tissue.

18. The method of claim 16, wherein the vacuum cavity comprises a first vacuum cavity, the housing further comprises a second vacuum cavity, and advancing comprises advancing the needle electrode to penetrate the tissue in at least one of the first and second vacuum cavities.

19. The method of claim 15, wherein the vacuum cavity comprises a first vacuum cavity that defines a first depth, wherein the housing further defines a second vacuum cavity that defines a second depth and a third vacuum cavity that defines a third depth, wherein the first, second and third depths are different from one another, wherein applying vacuum pressure comprises applying vacuum pressure to at least one of the first, second and third vacuum cavities, and wherein advancing an electrode comprises advancing a needle electrode to penetrate tissue in at least one of the first, second and third vacuum cavities.

20. An implantable medical device comprising:
a device housing defining first and second vacuum cavities and one or more vacuum ports for application of vacuum pressure to draw tissue into at least one of the first and second vacuum cavities; and
an electrode that is movable into at least one of the vacuum cavities of the device housing to contact the tissue drawn into the respective vacuum cavity, wherein a depth of at least one of the first and second vacuum cavities is selected to permit deployment of the electrode at a selected layer of the tissue.

21. The device of claim 20, wherein the electrode comprises a needle electrode that is movable into at least one of the first and second vacuum cavities to penetrate the tissue drawn into the respective vacuum cavity.

22. The device of claim 21, further comprising an electrical stimulator, positioned within the device housing, that is coupled to the needle electrode to deliver electrical stimulation to the tissue.

23. The device of claim 20, wherein the first and second vacuum cavities have different depths, and wherein the different depths are selected to permit deployment of the needle electrode at different, selected layers of the tissue.

24. The device of claim 20, wherein the first vacuum cavity defines a first depth and the second vacuum cavity defines a second depth different than the first depth, wherein the first depth is selected to permit deployment of the electrode at a first selected layer of the tissue and the second depth is selected to permit deployment of the electrode at a second selected layer of the tissue different from the first selected layer of the tissue.

25. The device of claim 24, wherein the device housing comprises a third vacuum cavity defining a third depth different from the first and second depths, wherein the third depth is selected to permit deployment of the electrode at a third selected layer of the tissue different from the first and second selected layers of the tissue, and wherein the electrode comprises a needle electrode movable into at least one of the first, second and third cavities.

26. The device of claim 24, wherein the first cavity and the second cavity are axially aligned with each other, and wherein the third cavity is off-axis from the first and second cavities.

27. A method comprising:
applying vacuum pressure to at least one of a first and second vacuum cavity in an electrode assembly housing to draw tissue into the respective vacuum cavity;
advancing an electrode that is movable into at least one of the first and second vacuum cavities of the housing to contact the tissue drawn into the at least one of the first and second vacuum cavities, wherein a depth of at least one of the first and second vacuum cavities is selected to permit deployment of the electrode at a selected layer of the tissue; and
delivering electrical stimulation to the tissue via the electrode.

28. The method of claim 27, wherein the electrode comprises a needle electrode, and advancing comprises advancing the needle electrode into at least one of the first and second vacuum cavities to penetrate at least a portion of the tissue drawn into the respective vacuum cavity.

29. The method of claim 28, further comprising delivering the electrical stimulation from an electrical stimulator positioned within the housing, the electrical stimulator being coupled to the needle electrode to deliver electrical stimulation to the tissue.

30. The method of claim 27, wherein the first vacuum cavity defines a first depth and the second vacuum cavity defines a second depth different than the first depth, and wherein the first depth is selected to permit deployment of the electrode at a first selected layer of the tissue and the second depth is selected to permit deployment of the electrode at a second selected layer of the tissue different from the first selected layer of the tissue.

31. The method of claim 30, wherein the electrode assembly defines a third vacuum cavity defining a third depth different from the first and second depths, wherein the third depth is selected to permit deployment of the electrode at a third selected layer of the tissue different from the first and second selected layers of the tissue, wherein applying vacuum pressure comprises applying vacuum pressure to at least one of the first, second and third vacuum cavities, and wherein advancing an electrode comprises advancing a needle electrode into at least one of the first, second and third cavities.

32. The method of claim 31, wherein the first cavity and the second cavity are axially aligned with each other, and wherein the third cavity is off-axis from the first and second cavities.

* * * * *